(12) United States Patent
Debreczeny

(10) Patent No.: US 8,405,033 B2
(45) Date of Patent: Mar. 26, 2013

(54) OPTICAL SENSOR FOR RAPID DETERMINATION OF PARTICULATE CONCENTRATION

(75) Inventor: Martin P. Debreczeny, Danville, CA (US)

(73) Assignee: BugLab LLC, Concord, CA (US)

( * ) Notice: Subject to any disclaimer, the term of this patent is extended or adjusted under 35 U.S.C. 154(b) by 26 days.

(21) Appl. No.: 13/194,387

(22) Filed: Jul. 29, 2011

(65) Prior Publication Data

US 2012/0194800 A1 Aug. 2, 2012

Related U.S. Application Data

(60) Provisional application No. 61/401,887, filed on Aug. 20, 2010, provisional application No. 61/400,580, filed on Jul. 30, 2010.

(51) Int. Cl.
*G01J 5/08* (2006.01)
(52) U.S. Cl. .................................... 250/343; 250/338.1
(58) Field of Classification Search ................ 250/338.1
See application file for complete search history.

(56) References Cited

U.S. PATENT DOCUMENTS

| 5,483,080 | A | 1/1996 | Tam |
| 6,046,814 | A * | 4/2000 | Karlsson et al. ............... 356/437 |
| 6,573,991 | B1 | 6/2003 | Debreczeny et al. |
| 7,100,462 | B2 | 9/2006 | Gronvall |
| 2005/0173635 | A1* | 8/2005 | Smith ...................... 250/339.13 |
| 2006/0152730 | A1 | 7/2006 | Schneider |
| 2008/0061237 | A1* | 3/2008 | Franz et al. ............... 250/339.01 |
| 2008/0204716 | A1 | 8/2008 | Trainer |
| 2008/0221711 | A1 | 9/2008 | Trainer |
| 2009/0075248 | A1 | 3/2009 | Debreczeny et al. |

OTHER PUBLICATIONS

PCT Search Report for Application No. PCT/US2011/045924.

* cited by examiner

*Primary Examiner* — David Porta
*Assistant Examiner* — Marcus Taningco
(74) *Attorney, Agent, or Firm* — Quine Intellectual Property Law Group, P.C.; Gary Baker

(57) ABSTRACT

This invention provides methods and devices to measure particle suspension concentrations through the side wall of a container. Particle back-scatter readings are taken at light wavelengths that do not travel far through the medium. Detected scatter is related to actual particle concentration or standard O.D. values. The methods and devices allow particle concentration readings through containers not normally intended for use in such assays.

45 Claims, 19 Drawing Sheets

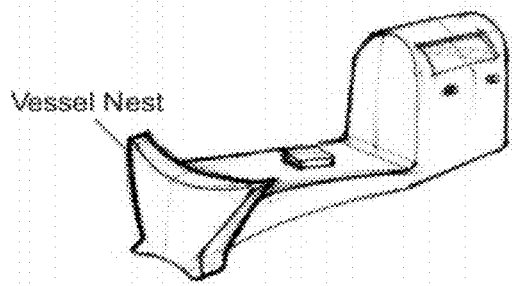
Fig. 5G1
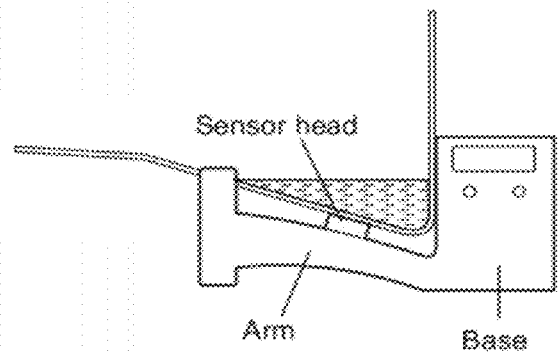
Fig. 5G2
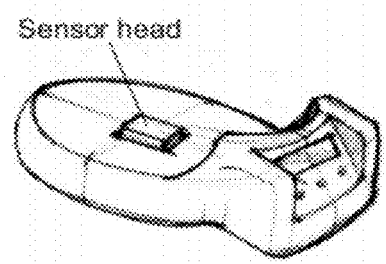
Fig. 5H1
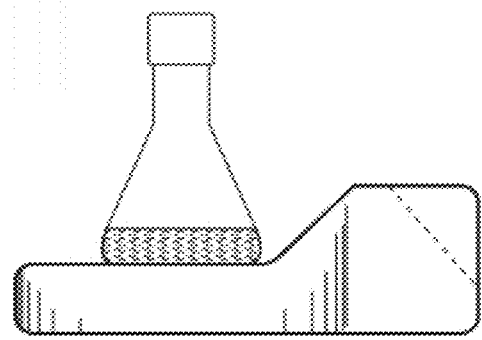
Fig. 5H2

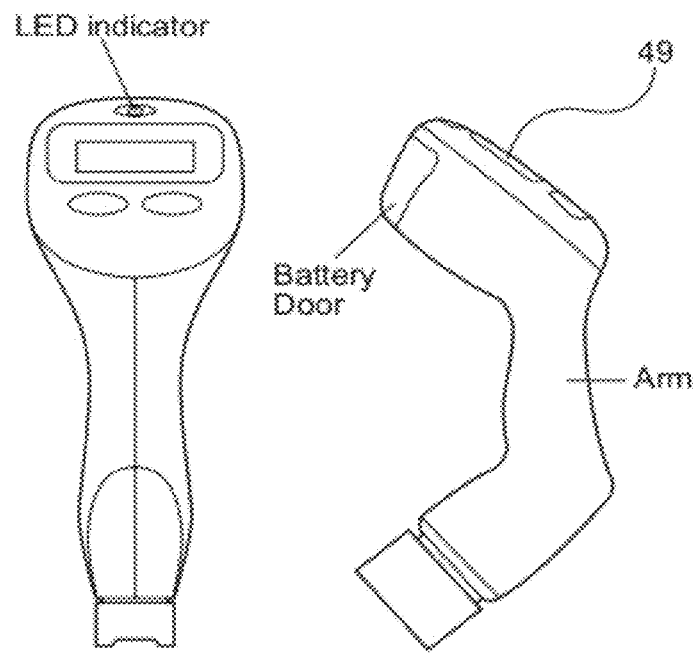
Fig. 5I1            Fig. 5I2
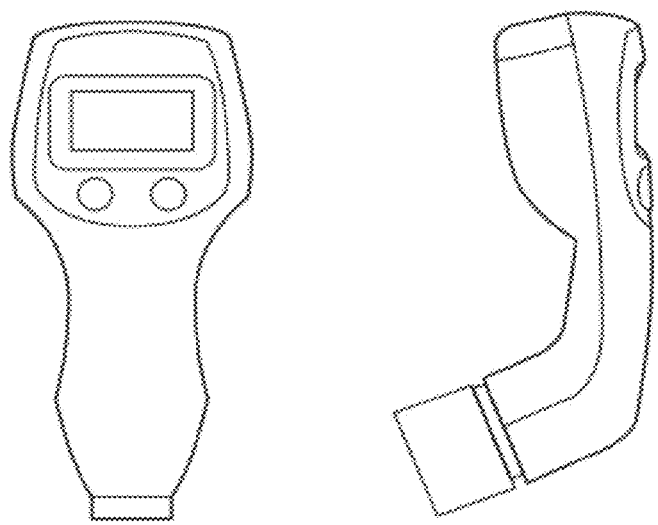
Fig. 5J1            Fig. 5J2

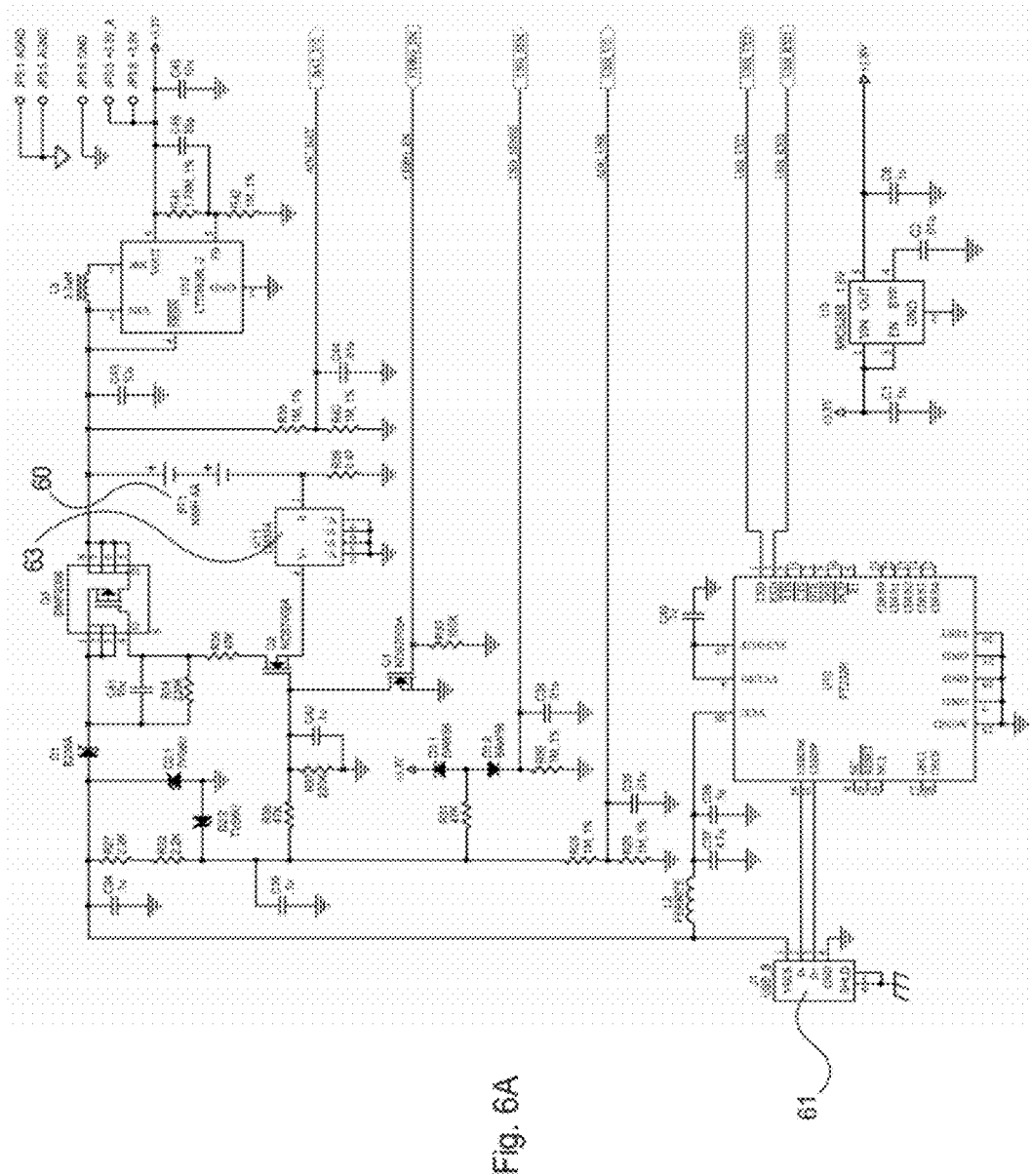

OPTICAL SENSOR FOR RAPID DETERMINATION OF PARTICULATE CONCENTRATION

CROSS-REFERENCE TO RELATED APPLICATIONS

This application claims priority to and benefit of a prior U.S. Provisional Application No. 61/401,887, Optical Sensor for Rapid Determination of Particulate Concentration, by Martin Debreczeny, filed Aug. 20, 2010, and a prior U.S. Provisional Application No. 61/400,580, Optical Sensor for Rapid Determination of Particulate Concentration, by Martin Debreczeny, filed Jul. 30, 2010. The full disclosure of the prior applications are incorporated herein by reference.

FIELD OF THE INVENTION

Methods and devices for measuring particulate concentrations in a suspension held in a container. Devices are configured to accommodate and compliment typical laboratory containers and other equipment. Measurements of particle concentration are made, e.g., through the wall of the container by detection of back-scattered light. Detected signals can be related to, e.g., particle concentration or standard O.D. 600 nm values.

BACKGROUND OF THE INVENTION

In U.S. Pat. No. 7,100,462 "Self Adjusting Sensor Mounting Device", methods and devices are described for reproducibly mounting a sensor to a wide variety of cylindrical and flat surfaces in a manner that automatically compensates for the curvature of the mounting surface.

In US patent application 2009/0075248, "Particle sensor with wide linear range", methods and devices are described for measuring particulate concentration in vessels, where the response from multiple source-detector pairs is combined to provide a linear response over a wide range of particle concentrations. Also described, are methods and devices for confining the measurement to a specific volume within the medium, as methods and devices for performing rapid sequential measurement of particle concentration in multiple vessels.

In view of the above, a need exists for devices that can read particulate concentrations directly from the containers in which they are held or cultured. It would be desirable to have methods to read particulate concentrations in atypical environments or from containment not specifically designed to be used in analytical procedures. Benefits could also be realized from methods and devices capable of reading particle concentrations in shallow samples and without the need to dilute the sample. The present invention provides these and other features that will be apparent upon review of the following.

SUMMARY OF THE INVENTION

An optical sensor for rapidly, accurately, and non-invasively measuring the concentration of particles suspended in a medium held within a variety of vessel types is disclosed. The sensor consists of one or more light sources and one or more detectors contained in a housing. The sensor is interfaced to a vessel containing a medium with suspended particulate matter. The one or more light sources are directed through the vessel wall into the medium, scattered by the particulate matter, and then some portion of the scattered light is detected through the vessel wall by the one or more detectors. The light sources and detectors are selected to emit and detect light in a spectral region that is substantially absorbed by the medium, thereby confining the measurement to a restricted volume within the medium. Methods and devices for directing as well as ensuring proper orientation of the sensor relative to the vessel prior to and during measurement are also described. Additionally described are methods and devices for accurately determining the particle concentration over a wide range of particle concentrations.

Accordingly, several objects and advantages of the present invention are:
a) the sensor response has a wide range of sensitivity to changes in a function dependent on particle concentration,
b) the sensor response has low sensitivity to objects outside of a selected measurement region,
c) the sensor has low sensitivity to changes in ambient lighting conditions,
d) the sensor is easily and rapidly calibrated during manufacturing,
e) the sensor calibration is easily and rapidly checked and adjusted by the user, and
f) the sensor response has low sensitivity to changes in temperature.

Additional objects and advantages of the present invention for the specific embodiment in which the sensor is held or affixed externally to a container holding a liquid culture for the purpose of measuring the biomass:
a) the need to withdraw samples from the culture in order to determine biomass is eliminated,
b) the risk of contaminating the liquid culture with foreign matter is eliminated,
c) multiple different containers can be monitored with the same sensor without interrupting the growth of the cultures or risking exposure of the cultures to foreign matter,
d) accurate measurement of biomass is enabled even in small vessels filled with minimal amounts of medium,
e) the need to interrupt vessel agitation during biomass measurement is reduced or eliminated,
f) the measured value of the biomass in the liquid culture is accurate despite variations in window thickness between different containers, and
g) means are provided to ensure that the sensor position relative to the container and/or medium is such that an accurate result will be provided.

Methods of the invention can include, e.g., determining the concentration of at least one type of particle in a medium by passing radiation (e.g., light) originating from at least one source into the medium, wherein the radiation is substantially absorbed by the medium, detecting light scattered by particles within the medium using at least one detector, measuring at least one signal corresponding to the portion of radiation detected by one of said detectors that originated from one of the light sources, and relating at least one of the signals to the concentration of at least one type of particle. Typically, detecting the radiation is accomplished by positioning a sensor externally to a container that holds the medium, the container being substantially transparent, or providing a transparent window on the container.

The method can further include a means of detecting the position or orientation of the sensor relative to the container, or providing means of reducing the sensitivity of the combined result to variations in the thickness of the window. The method can include providing means of detecting the position and orientation of the sensor relative to the container. For example, one or more position switches can provide means to determine the position or orientation of the sensor relative to the container. Optionally, one or more capacitance switches can provide a means to determine the position or orientation of the sensor relative to the container. For example, the capacitance switches can be used to determine that a sufficient volume of medium is present in the vicinity of the sensor for a particle concentration measurement to be made accurately. Alternately, the position or orientation can be determined using optical components, such as a light source and detector.

In certain embodiments, radiation sources and sensors are positioned symmetrically about their counterpart. For example, at least two sources can be positioned symmetrically with respect to a detector component, or visa versa. Such devices can reduce inconsistent detections or detect positioning errors during analysis of a sample. For example, the two symmetrically positioned optical elements can provide a means of determining whether sufficient medium is present in order to make an accurate measurement of particle concentration.

In preferred embodiments, the radiation is detected as back-scattered light and the result is converted to an optical density readout. In many embodiments, absorbing components of the medium being analyzed include water. In a preferred embodiment, the distance between a source and detector is matched to the mean path for absorption by the medium of radiation emitted by the source.

In many embodiments of the methods, a means is provided for subtracting a measurement of blank media from a measurement of media containing particulate matter. In preferred embodiments, coefficients can be input or determined relating detected signals to the particle concentration measurement. In the methods, it is beneficial to provide a means of checking for or correcting for proper instrument performance, e.g., by providing duplicate measurements, measurements from different light paths, comparison to standard references, comparison to controls, etc.

In certain methods, a guide is provided for guiding the sensor into a desired alignment with the container. In preferred embodiments, the guide is readily removable and replaceable. In preferred embodiments, the guide includes a U or V-shaped feature in one dimension and a substantially flat feature in a second dimension, e.g., to align the sensor relative to the axis of a sample container. In some embodiments, magnetic force is used to hold the guide against the sensor. In many embodiments, the guide includes an element that is deformable under pressure, so that multiple different container sizes may be automatically accommodated. In some embodiments, the sensor is surrounded by a shell that helps to properly orient the sensor onto the vessel. In many methods of the invention, audio or visual cues are provided to guide an operator in finding or maintaining the position of the sensor relative to the container. In some embodiments of the invention the multiple sensors are interfaced with a single controller, allowing the particle concentration to be determined in multiple vessels without requiring sensor repositioning.

In one embodiment, the sensor consists of at least one near-infrared laser light source emitting near 1310 nm, and at least one optical reflectance detector. The sensor is held against the wall of a vessel, such as a shake flask, containing cells or microorganisms suspended in an aqueous medium. Laser light is directed through the wall of the vessel into the medium and is scattered by the cells or microorganisms. In addition to scattering, the 1310 nm light is partially absorbed by water in the medium. The relationship between Optical Density and the reflectance signal measured by the sensor is stored as a calibration in the instrument, which may vary according to the type of cell or microorganism being grown in the medium. In some embodiments, a baseline offset is provided to allow compensation for the contribution of the medium to the measured Optical Density.

In preferred embodiments, the radiation source emits light at a frequency ranging from about 650 nm to 2200 nm, from 700 nm to 2000 nm, from 800 nm to 1800 nm, from 1000 nm to 1600 nm, or about 1500 nm. In preferred embodiments, the source provides light radiation in the infrared wavelengths. In some embodiments the source provides radiation ranging between 1150 nm and 1350 nm. In other embodiments, the source emits light at a wavelength between 920 and 1150 nm, or between 350 and 1900 nm.

In some embodiments a second reflectance or scatter detector is arranged symmetrically with respect to a first reflectance detector, as a means to determine proper sensor positioning. Comparison of the processed signals from the two detectors ensures that the measurement is being made from within a sufficient depth of fluid to provide accurate determination of particle concentration. In some embodiments additional detectors are spaced at a different distance from the laser to extend the linear range of response to changes in particle concentration.

In some embodiments the reflectance detectors are held at the end of apertures constructed from a material, which is strongly absorptive of light emitted by the source. The optic axes of the laser and reflectance detectors may be oriented parallel to each other, and the divergence and collection angles restricted, so as to minimize sensitivity to vessel wall thickness and restrict the measurement volume within the medium.

In some embodiments, the sensor includes at least one position detector. The position detector(s) on the sensor face provide a means of determining when proper sensor positioning has been achieved, and can also be used to trigger a measurement and to help determine whether a measurement has been successfully completed. In some embodiments the position sensor includes at least one position switch. In other embodiments the position sensor includes at least one capacitance sensor. In some embodiments the capacitance sensor is used to determine whether sufficient medium is present in the vessel in proximity to the sensor in order for an accurate measurement to be collected. In other embodiments, the position sensing is performed using optical components.

In some embodiments the concentration is reported as an Optical Density (OD) such as would be reported by a spectrophotometer at a particular wavelength (e.g., 600 nm) through a 1 cm path length cell containing a dilute solution of the medium, after multiplication by the dilution factor. In some embodiments the concentration is reported as standard turbidity units (e.g., NFUs), dry or wet weight per volume (e.g., g/mL), cells counts per volume (e.g., cell/mL), or any user-defined value, related to particle concentration. In some embodiments the type of units in which the result is reported is user-selectable The light scatter by particles in the methods can be detected by any appropriate type of detector. For example, detection can be by a photomultiplier tube, photodiode, or photodiode array. In preferred embodiments, at least one of the detectors employs silicon in active detector area of its sensor. In some embodiments, at least one of the detectors employs InGaAs in its active area.

The illumination source in the methods can be any appropriate means, such as, e.g., a laser, a tungsten lamp, mercury vapor lamp, LED, diode lasers and/or the like. In certain embodiments, a monitoring diode is built into the laser package, and is used to compensate for changes in radiant flux emitted by the laser, e.g., a laser monitoring detector is used to directly measure the output of the laser, providing a means of compensating for intensity variation such as may be caused by temperature fluctuations.

In some methods of the invention, a bar code scanner is built into the device and used to track the measurements, e.g., the identification of samples. In the methods, it can be useful to have information transferred wirelessly, e.g., the measured particle concentration can be wirelessly transferred to an ancillary or peripheral device.

In another embodiment of the methods, a concentration of at least one type of particle in a medium is determined by positioning a sensor next to a container holding the medium, passing radiation originating from at least one source through the container wall into the medium that substantially absorbs the radiation, detecting with at least one detector a signal relating to radiation reflected from within said medium back through the container wall, and relating the detected radiation signals to the concentration of a particle in the medium.

The inventions include devices for detecting and measuring the concentration of particles in a container. In one aspect, the device for determining the concentration of at least one type of particle in a medium includes, e.g., a housing containing a sensor, including at least one radiation source and at least one radiation detector positioned to collect source radiation scattered by particles within said medium, wherein the radiation emitted by the source is substantially absorbed by the medium. The device further comprises a controller for controlling the radiation sources, and for measuring at least one of the signals corresponding to the portion of radiation detected by one of the detectors that originated from the radiation sources. The device typically also includes a processor configured to relate at least one of the signals to a concentration of at least one type of particle.

In preferred embodiments, at least one of the radiation sources is modulated in amplitude or frequency. In such cases, it can be beneficial to provide means for reducing the dependence of said detector measurement on the timing of the measurement relative to the source modulation cycle, e.g., by configuring the device so that the rate at which the detector signal is measured is substantially greater than the rate at which the sources is modulated. In a certain embodiment, quadrature slope correction is employed as part of the detector demodulation algorithm.

Power for the device can be from any appropriate source. For example, power can be from an AC outlet, batteries, photovoltaics, etc. In preferred embodiments, the power for the controller and processor is provided by batteries, e.g., low self-discharging Nickel Metal Hydride (LSD-NiMH) type.

Due to the environment in which the devices typically employed, it can be useful to provide means for making the device enclosure substantially resistant to water ingress.

The device sensor can be configured to be well-adapted to taking measurements from any number of different containers or vessels. For example, the sensor housing can be attached to a disposable fermentor, bioreactor, flask, bottle, bag, or tube. The sensor housing can be affixed to a vessel, providing the capability of making multiple measurements without the need for reapplication of the sensor to the vessel. Multiple sensors can be interfaced with the same controller. In some embodiments, the sensor housing is designed to be disposable. Radiation sources or detectors can be fiber optical components optically linked to electro-optical components that are physically separated from said housing. In some embodiments fiber optics are used to convey light between the sensor and electro-optical components. In some such embodiments fiber optics splitters and/or switchers are used to multiplex the electro-optical components between multiple fibers.

The controller can be any appropriate type. The device controller can employ a Complex Programmable Logic Device (CPLD).

The device can be configured to take particle concentration measurements. In preferred embodiments, the time required for measurement of particle concentration is three seconds or less. In other embodiments, the measurement time is variable, as determined by a metric related to measurement accuracy. In another aspect, signals are combined from source-detector pairs with at least two different separation distances. In another aspect, at least two of the radiation sources have substantially different emission wavelengths. In certain devices, the source wavelengths can be selected according to the separation between the source-detector pairs.

The devices can be configured to consistently collect accurate measurements from samples in unusual containers or unusual conditions for analysis. For example, when the amount of medium in front of the sensor varies over time (e.g., a shaker flask), and the signals can be collected rapidly enough to capture this variation. Where there are different amounts of medium present in one or more samples, the signals collected can be proportionately modulated by the processor, e.g., the ratio of signals collected with different amounts of sample fluid present can be considered in determining the correct particle concentration.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "feed" can include mixtures of feed, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

As used herein, the term "radiation" is used interchangeably with "light".

A "mean absorption path length" is the average distance covered by a photon within a medium before it is absorbed by the medium.

A "sensor" of the methods and devices is a device component comprising at lease one light source-detector pair in functional association.

As used herein, "modulated" means to vary the amplitude, frequency, or phase of a light source.

BRIEF DESCRIPTION OF THE DRAWINGS

FIG. 5a-j depict different enclosures and some of their modes of use by the present invention.

FIGS. 6a-c are electronic schematics employed in one embodiment of the present invention.

DETAILED DESCRIPTION

Figure 1A:
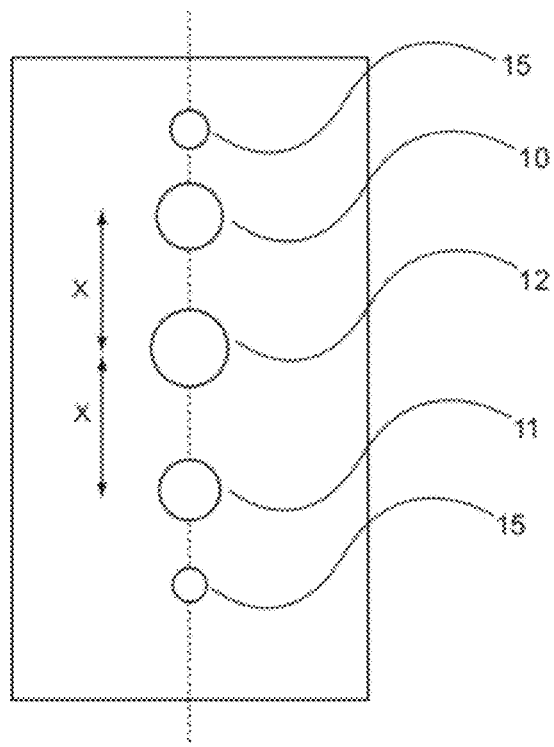
FIGS. 1a-f depict arrangements of optical and position sensing components in sensor heads of the present invention.

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments as suggested in the present description, and may be satisfactorily applied for the measurement of any material which may exhibit similar behavior that are also intended to be encompassed within the spirit and scope of the invention.

The detailed description set forth herein will make reference to the measurement of biomass in a liquid culture. The term "biomass" as used in this patent application, refers to the concentration of biological material, such as cells or microorganisms. What is meant here and elsewhere in the patent application by "concentration" is the number of a type of particle, weight of a type of material, or volume of a type of material found in a given volume of a medium.

Optical Density (OD) is defined as:

$$OD = -\log_{10}\left(\frac{I}{I_0}\right)$$

where light intensities are measured after transmission through a sample (I) and in the absence of the sample ($I_0$). It is common in the biofermentation field to measure and refer to biomass according to the optical density measured at a particular wavelength, such as 600 nm ("OD600"), through a 1 cm path length cuvette, with a commercial spectrophotometer. When measuring OD using a spectrophotometer it is necessary to dilute the sample to have an OD in a linear range of response (commonly OD<1, but more ideally OD between 0.05 and 0.2) and then scale the measured OD by the dilution factor. This type of measurement is herein referred to as "Offline OD" measurement, to distinguish it from the real-time ("Online") measurement allowed by the methods and devices for the present invention. For mono-disperse cells a linear relationship between biomass and OD generally holds.

The method(s) and instrument(s) of the present invention may also find application in liquid suspensions of solids other than biomass as well as in solutions. For example, the particulate content in milk, the rate of polymerization in a chemical system or the turbidity of water may be measured by application of the method(s) and/or instrument(s) of the present invention. Similarly, the present invention may be utilized to determine the amount of gas in a liquid phase, such as the concentration of gas bubbles in a liquid medium. In addition, the attenuation of radiation by absorption may be used to measure the concentration of components dissolved in solution, by application of the present invention.

The method and instruments of the present invention may also be useable in the gas phase. For example, in industrial plants using smokestacks, the amount or concentration of a specific component of the effluent gas may be measured by application of the present invention. As another example, the present invention may be used to measure the particulate content of a gas for the purpose of smoke or fire detection. As yet another example, the present invention may be used to measure the concentration of a particular component of a gas, such as the concentration of carbon dioxide in a mixture of gases or the density of fog or smoke in the flight path of an airplane.

In addition, the method(s) and/or instrument(s) of the present invention may be utilized to monitor materials in the solid state and to monitor transformation of materials between states. For example, the present invention may be used to measure the concentrations of oxygenated and deoxygenated hemoglobin in tissue. As another example, the present invention may used to monitor the conversion of a liquid to the solid state, such as gel formation. Thus, although the hereinafter-set-forth descriptions often refer specifically to the measurement of the biomass in a liquid culture, it will be appreciated that the method(s) and instrument(s) of the present invention are also applicable in other liquids and in gas and solid media applications.

Description of Inventive Methods

The present methods are generally directed to techniques of illuminating a container of particulate suspension from the outside and determining the particulate concentration in correlation to the amount of light scattered back. By employing an interrogation light wavelength that does not penetrate far into the media of the suspension the requirement of diluting the sample can be avoided. Further, shallow interrogation can mitigate problems associated with moving (e.g., shaking) samples and assay of samples with non-uniform depth.

In one embodiment, the method for determining the concentration of particles in a medium includes providing the medium in a walled container, irradiating the medium with a light source through the wall with a wavelength of light, detecting light scattered by the particles in the medium using a detector positioned outside the container wall and correlating the detected light to the concentration of the particle. In preferred embodiments, the light does not penetrate substantially into the medium. The interrogation light is typically in the infrared spectrum. In preferred embodiments, the light source shines into the container through a wall substantially transparent to the light wavelength, and the light is scattered back through the wall to a detector near the light source and aligned in substantially the same direction as the light source.

In another exemplary embodiment, the method determines the concentration of particles in a container of medium. The method includes the steps of positioning a sensor next to a container holding the medium, passing light originating from at least one light source through the container wall into the medium, wherein the medium absorbs the light as characterized by a mean absorption path length, detecting a light signal through the wall with a detector, wherein the spatial separation between the light source and first detector is within a factor of 10 of the mean absorption path length, and wherein the signal is from light reflected from within the medium, and correlating the detected signal to the concentration of the particles in the medium.

In typical embodiments, the light is infrared, the container is a culture flask, the media is aqueous, and the particles are cells. The light source and detector are typically arranged in a sensor housing across a surface and aligned so the light is transmitted in a path describing an acute angle from the direction of detector detection (e.g., optical axis of a conical detection zone for the detector).

The container of media is typically a container designed to hold or store media, but not typically a container normally employed to function with spectroscopic equipment in, e.g., a quantitative analysis. The containers in the present methods are typically, e.g., a shaker flask, a T-flask, a centrifuge tube, a test tube, a roller bottle, a fermentor, a bioreactor, a stir flask, a carboy, a bag, a media bottle, a multiwell plate, a petri dish, a syringe, a pipette and/or the like. In a typical embodiment, the container is not a cuvette (e.g., from a spectrophotometer or fluorometer) and is not a spectroscopic flow cell (e.g., from an assay device).

Where the media is aqueous, the light wavelength is typically an infrared (IR) wavelength. This is because IR wavelengths are well scattered by particles typically of interest and such wavelengths are substantially absorbed by shallow depths of water, with the benefits described above. The light source wavelength in the methods can also depend to some extent on the optical qualities of the container wall in a particular instance. Other useful ranges of light source wavelengths range from less than 650 nm to more than 2000 nm, from about 700 nm to about 1500 nm, from 800 nm to about 1300 nm. In certain embodiments the preferred wavelength is about 1310 nm. In other applications the light sources emits light between 1150 and 1350 nm, between 920 and 1150 nm, or between 1350 and 1900 nm. In the context of other media, such as organic solvents, other optimum interrogation wavelengths are available, e.g., wherein the particles of interest scatter the light well, and the solvent limits penetration of the light to desired shallow depths.

It is desirable in many embodiments of the methods to determine particle concentrations that the interrogating light wavelength not penetrate too far into the media of the particle suspension. This can help avoid inaccuracies resulting from, e.g., light reflecting from the opposite wall of the container, light reflecting off an air interface with the media, and variance due to sample depth instead of particle concentration. In the methods, it is typically preferred that the wavelength of light be at least 50% absorbed by the media within the first 10 cm, 5 cm, 2 cm, 1 cm, 0.5 cm, 0.25 cm or 0.1 cm of the light path through the particular medium. In a typical embodiment, the mean absorption path length matches the source-detector separation within a factor of 5. In the methods, it is typically preferred that the wavelength of light be absorbed by the media with a mean absorption path length that is within a factor of 10, 5, 2, or 1.5 of the separation between the source and detector. In a typical embodiment, the mean absorption path length matches the source-detector separation within a factor of 5. Matching of the mean absorption path length with the source-detector separation "within a factor of" X, means that either the mean absorption path length, when multiplied by any number between 1 and X, will match the source-detector separation, or the source-detector separation when multiplied by any number between 1 and X, will match the mean absorption path length.

In the methods, it is useful to have the light source and detector on the same side of the container for the analysis. In this way, the scattered light path is not dependent on the container to provide consistent and adequate geometry. That is, a significant benefit of the present methods is that particle detection does not depend on the shape or size of the container holding the media. For example, as long as the media to be tested is in contact with the inside wall of the container at a certain position, the methods allow the reading device to realize an appropriate interaction with the media. The media does not have to be withdrawn or diluted. It matters little what is the shape or size of the container or whether the container is full. In many embodiments, the detector and light source are mounted in a device sensor with their objective aperture in a common plane and directed in substantially the same direction. In preferred embodiments, the light source and detector are arranged so that light emanating from the light source is scattered by particles in the media and returned to the detector describing an angle of from less than 5 degrees to 45 degrees, from 10 degrees to 35, from 15 degrees to 30 degrees or about 25 degrees.

The light source may radiate light in, e.g., a beam or cone, and the detection zone visible to the detector can be described by, e.g., a cylinder or cone. In preferred embodiments, the optical axis of the light source and the optical axis of the detector detection zone are substantially parallel. In other embodiments the axes can converge or diverge from each other at an angle ranging from about 1 degree to 45 degrees, from 3 degrees to 30 degrees, from 5 degrees to 20 degrees or about 10 degrees.

The particles detected in the methods can be any of interest, e.g., in a reasonably uniform suspension. The particles of interest are typically from the fields of materials science or biological sciences. Typical particles of interest in the present methods include, e.g., bacteria, fungi, animal cells, plant cells, polymer particles, nanoparticles, sol gels, viruses, and the like.

The methods include means of positioning and confirming the position of a light-detector sensor system in relation to the container and media of interest. Uniform and optimal positioning of the sensor can be important to the precision, accuracy, sensitivity and consistency of particle concentration measurements in the methods. Position sensors and alignment guides of the inventive devices are discussed at length below.

The methods include provision of two or more detectors in functional relation to one or more light sources. In the methods, positioning of the sensor, uniformity of the media components, uniformity of the media depth and uniformity of the container wall can be suggested by comparison of signals returned from two or more detectors at different positions. The detectors can be positioned symmetrically or asymmetrically relative to the light source. For example, two symmetrically positioned detectors elements can be positioned to provide a means of determining whether sufficient medium is present in order to make an accurate measurement of particle concentration. In many methods, distance between the light source and detector is matched to the mean absorbance path length by the medium of the light wavelength. In preferred embodiments, the distance between the light source and detector is from 0.5 mm or less to 100 mm or more, from 1 mm to 75 mm, from 5 mm to 50 mm, from 10 mm to 35 mm, or about 6 mm.

Once scattered light is returned to the detector, the associated signal can be correlated with other useful parameters such as optical density (OD) values or particle concentration. The methods can optionally be used to quantitate the amounts of the particles of interest present in the sample. For example, in one class of embodiments, an intensity of a signal scattered back to the detector is measured and correlated (e.g., through a standard formula determined through regression analysis) with a quantity of the corresponding particles of interest present. The standard formula can then be used to calculate an unknown amount of particles in a sample based on the output signal intensity for that sample.

To increase the precision and accuracy of measurements, the light source can be monitored with a sensor that feeds back to the controller, which instructs compensating changes in radiant flux emitted by the light source, thus stabilizing the light irradiation. Another way to enhance the accuracy of particle concentrations in the methods is to take a blank reading of media without particles and subtracting the blank reading from a measurement of the media containing the particle.

In a particular embodiment, samples can be identified and tracked employing components of the inventive device acting as a bar code scanner. For example, the light source can be a laser and light reflected back to the detector during a sweeping motion across a bar code decal can be detected and interpreted by the processor to identify a sample.

Description of Device Embodiments

The devices of the invention are generally directed to paired light sources and sensors arranged to interrogate a sample of particles in a medium through the walls from one side of a container. For example, the devices for determining the concentration of particles in a medium, can include a housing containing a sensor, a light source in the sensor, a detector in the sensor and positioned to detect a signal of source light wavelengths scattered by particles within the medium, and a processor configured to correlate the detected signal to the concentration of particles. Typically the light wavelength emitted by the source is selected to be absorbed without overly extensive penetration into the medium. The device typically comprises a controller configured to measure the detected signals and to control the light sources.

It can be beneficial to make the light source distinctive over background light, and render it complimentary to certain detector circuitry. In a preferred embodiment, the light source of the device is modulated in amplitude or frequency. In such a case, accuracy can be enhanced wherein the detector reading frequency is different from the light interrogation frequency, e.g., thus avoiding problematic beat frequencies, and other interference. In preferred embodiments the detector signals measurement rate is at least 4-fold, 10-fold or 100-fold, or more different (preferably greater), than the modulation rate of the light source. In certain embodiments, a quadrature slope correction is employed as part of a detector demodulation algorithm.

In situations where multiple particulate concentration readings are expected over some time period, it can be useful to affix the light-detector sensor housing to the vessel, thereby providing the capability of making multiple measurements without the need for reapplication of the sensor to the vessel. Typical vessels containing media and subject to particle concentration readings by the devices of the invention include, e.g., shaker flasks, a T-flasks, centrifuge tubes, test tubes, roller bottles, fermentors, bioreactors, stir flasks, carboys, media bags, media bottles, multiwell plates, petri dishes, syringes, pipettes and the like.

The sensors of the devices can have complex arrangements of one or more light sources paired with one or more detectors. For example, signals can be combined from two or more paired source-detectors with two different source-detector separations. The light source or detectors can be fiber optical components, which are optically linked to electro-optical components that are physically separated from the housing, wherein the device further comprises one or more additional detectors in functional relation to the light source. The device can include a second light source with a light wavelength different from the light wavelength of the first light source, e.g., to selectively detect a different particle type or compliment a different container or media. The light source wavelength can be selected according to the separation between the source and the detector, e.g., to tailor the light path length to the expected particle density or media absorbance.

In certain embodiments, the device is configured to provide particular desired characteristics, For example, the device controller can be configured to collect detected signals at least every 0.10 seconds, thereby allowing measurement of variation in the amount of medium or particles in front of the sensor as it varies over time. The processor can be configured to distinguish signals depending on an amount of medium present at the container. The processor can be configured to correlate a ratio of signals collected in the presence of different amounts of media sample to the particle concentration.

In preferred embodiments, the light source and detector are both directed in the same direction. In many embodiments, the source and detector are aligned within 1 degree, 2 degrees, 5 degrees, 10 degrees 20 degrees or 30 degrees of each other.

Sensor Optical Arrangement.

Embodiments of a sensor of the present invention are illustrated in FIGS. 1-5. Referring to FIGS. 1a-b, a sensor housing holds optical components and provides apertures into and out of the sensor. A laser is placed within an illumination aperture in the sensor housing. The illumination aperture may be used to limit the divergence of the laser beam in addition to serving as a mount for the optical components. In some embodiments the laser is focused by a lens that can also help limit the divergence angle of the laser. The laser depicted in FIG. 1b includes a ball lens with ~6 mm length, causing the laser to have a divergence of approximately 10 degrees. A laser monitoring detector provides a signal for measuring and/or controlling the laser radiant flux. The laser is directed through the wall or aperture ("window") of a vessel into a medium. The vessel window should be at least partially transparent to light at the laser wavelength. Suitable vessels include flasks, bottles, tubes, fermentors, and bioreactors with window material made from such optically transparent materials as plastic (e.g. polyethylene terephthalate (PET), polycarbonate (PC)), or glass. The preferred embodiment described here is especially well-suited for thin-walled (<6 mm thick) vessels, such as is typically found in laboratory shake flasks, roller bottles, and tubes.

The front face of the sensor may be covered with a face plate that protects the sensor from the environment in which it is operated. The face plate should be constructed from a material that is transmissive to light emitted by the laser. In addition, the face plate may be absorptive to light at wavelengths other than the laser emission wavelength. An example of a suitable material for the face plate is Edmund Optic part number NT 43-954, which is transmissive to near infrared light but absorptive to visible light. In some embodiments a gasket is used to prevent the sensor from sliding easily against the vessel surface. When pressed against a vessel wall, the gasket may also be used to create a seal that prevents materials from occluding or affecting the optical measurement. In some embodiments, surrounding the face plate is a gasket groove used to contain the gasket. The gasket groove helps to prevent the gasket from moving and possibly obstructing the face plate.

After the laser has penetrated the vessel window, cells or microorganisms within the medium scatter the laser light, some of which is reflected back towards the sensor. Reflected light is detected by at least one reflectance detector. In the embodiment depicted in FIGS. 1a and b, two detectors 10 and 11 are placed symmetrically around the laser 12. The center-to-center distance between the laser and each detector is approximately 6 mm. The detectors are placed behind apertures 13 to limit the angle of the detection cone. The aperture depicted in FIG. 1b is approximately 5 mm long and 1.6 mm in diameter. As a result, the detection cone angle is approximately 18 degrees. Many other combinations of aperture length and diameter could be used to achieve the same or similar detection cone angles. Optionally, additional detectors 14 can be provided, e.g., as shown in FIGS. 1e and 1f.

In addition to being scattered by the contents of the medium, the laser wavelength is chosen so that it is partially absorbed by the medium itself. Water, being the principle constituent of all cell media and relatively invariant in concentration, is an ideal candidate for providing this partial absorption of the light source. The absorption by the medium needs to be low enough so that the light has a chance to scatter from cells in the medium and return to the detectors before being absorbed. On the other hand, the absorption needs to be high enough so that light scattered from the cells and then reflected by the vessel wall, objects external to the vessel, or non-cellular objects within the vessel, has a low probability of returning to a location within the vessel from which it can enter the detector apertures before being absorbed by the medium.

The relative geometry of the source and reflectance detectors will determine the desired absorption coefficient of the medium at the excitation wavelength. A source-detector separation of between 1 and 50 mm, is well suited for the present application. At shorter distances, the sensor may be overly sensitive to specular reflections from the surface of the vessel. At longer distances, the amount of light detected may be too small for accurate measurement, or may place a lower limit on the size of vessels or volume of media that can be measured. As a rule of the thumb, the source-detector distance and the mean absorption path length (defined as the inverse of the optical absorbance) of the laser by the medium should be roughly matched (within an order of magnitude). In the preferred embodiment depicted in FIG. 1, the source-detector distance is 6 mm, and the laser wavelength is 1310 nm. At this wavelength, the mean absorption path length in pure water is 6.4 mm (absorbance=1.56 cm−1).

Minimizing Sensitivity to Vessel Wall (Window) Thickness

Figure 1B:
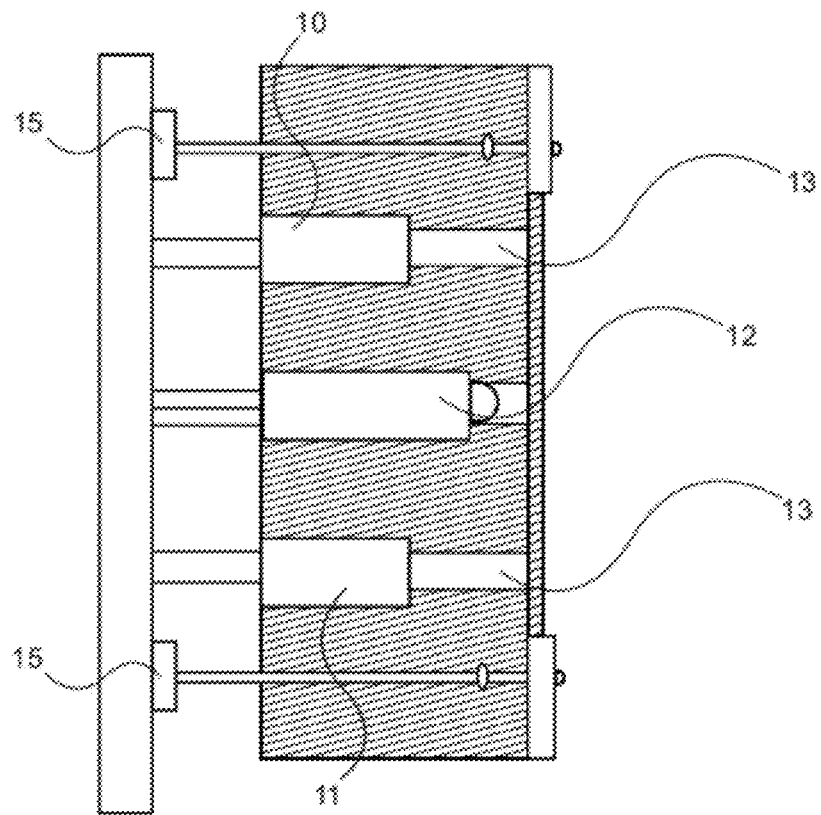

In the embodiment depicted in FIGS. 1a-b, the laser and reflectance detector components are positioned so that the optical axis of the laser beam is approximately parallel with the optical axis of the detection beam. Making the laser and detection beams parallel and restricted in aperture results in low sensitivity of the measured scattering intensity to vessel wall thickness. Further narrowing of the laser and detection apertures, and spacing the laser and detectors farther apart beyond what is depicted above and in FIG. 1b, may further reduce the sensitivity of the measured scattering intensity to vessel wall thickness. However, as the laser and detector apertures are decreased or the distance between the source and detector is increased, the strength of the scattering signal will be diminished, so a balancing of the wall thickness sensitivity with the desired signal to noise ratio may be necessary. The source-detector separation will also have an effect on the range of linear sensitivity of the reflected intensity with biomass, as discussed further below and in patent application number US 2009/0075248.

In some applications, the window thickness may be uniform enough or thin enough so that methods for overcoming sensitivity to window thickness will be unnecessary. One such application may be a sensor applied to a disposable bioreactor. In such cases, restriction of the source divergence angle and/or detector acceptance angle may be unnecessary. In such embodiments, the lenses and apertures described above may be excluded.

Sensor-Vessel Alignment

The position of the optical components relative to the vessel will affect the intensity of the reflected light reaching the detectors. As discussed further in Example 1, below, experiments were performed to determine this geometrical dependence. Some angular and positional degrees of freedom between the sensor and vessel are depicted in FIGS. 2a-d. Recommended geometric restrictions for maintaining the variation in reflected intensity to 5% or less for the particular embodiment of the invention described in example 1 are summarized in Table 1. Different (non-perpendicular) center values could be selected for any of the angular degrees of freedom. Such tilted geometries might have an advantage of reduced surface reflections, but may also suffer from increased sensitivity to window thickness.

TABLE 1

Sensor-Vessel Geometric Restrictions

| Geometric Parameter | Center Value | Allowed Deviation |
|---|---|---|
| $\theta$ | 0 degrees | ±5 degrees |
| $\gamma$ | 0 degrees | ±25 degrees |
| $\phi$ | 0 degrees | ±25 degrees |
| d | <3.0 mm | ±1.5 mm |

The two position sensors 15 depicted in FIGS. 1a and 1b are used to ensure that the desired sensor-vessel geometry has been achieved before a measurement is considered valid. The sensor is pressed up against the side (or window) of the vessel. The position switches protrude from the front of the sensor, and when simultaneously depressed, provide an indication that a valid measurement may be collected. In one embodiment the position switches requires travel of less than 0.3 mm in order to be activated, which will easily ensure adherence to the restrictions provided in Table 1. In the embodiment depicted in FIG. 1b, the position switches are located on a printed circuit board within the body of the sensor. Many suitable position switches are available, but one example is manufactured by Omron Electronic Components: part number B3U-1000P-B. This switch requires only 0.15 mm of travel with 150 grams of force in order to be activated, and has a conveniently small footprint (2.5×3.0×1.6 mm). A narrow rod is used to span the distance between the position switch and front of the sensor. One or more o-rings on the rod may be used to seal the cavity against moisture. This arrangement allows an inexpensive non-waterproof position switch to be used, while still providing protection of the instrument in wet environments.

In an alternate embodiment of the sensor, the position sensing is provided by one or more capacitance sensors. In one embodiment, the capacitance sensors are placed at the locations indicated in FIG. 1a. The capacitance sensors may further be selected and positioned so that they are only activated when sufficient medium is present beneath the surface of the window being measured. By requiring that both position sensors 15 depicted in FIG. 1 be located in close proximity beneath fluid filled regions of the vessel, the operator can be assured that the optical measurement will also be collected from within a fluid-filled region of the vessel.

Figure 10:
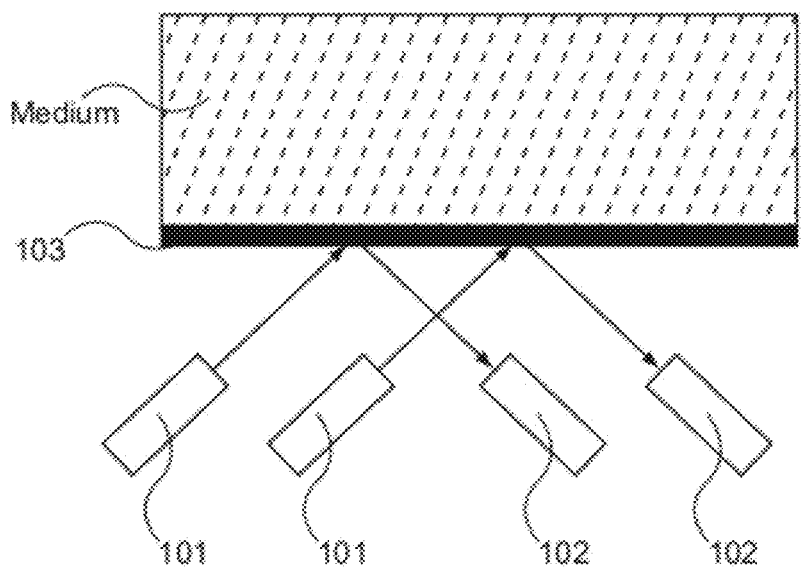
FIG. 10 depicts an arrangement of optical components for detecting the position of a sensor of the current invention relative to the surface of a vessel.

In yet another embodiment of the sensor, the position sensing is provided by one or more pairs of light sources and detectors. These source-detector pairs may be angled towards each other to detect surface (specular) reflections. The source divergence and detector acceptance angles are restricted so that only when the vessel surface 103 is in the desired orientation relative to the sensor, will a threshold level of surface reflection be detected. One such embodiment, depicted in FIG. 10, includes two source 101-detector 102 pairs. The two source-detector pairs are arranged such that only when $\theta, \phi, \gamma$, and d are within a selected range, such as that provided in Table 1, will threshold levels of reflectance be simultaneously detected by both detectors.

Alignment Guide

Figure 3A:
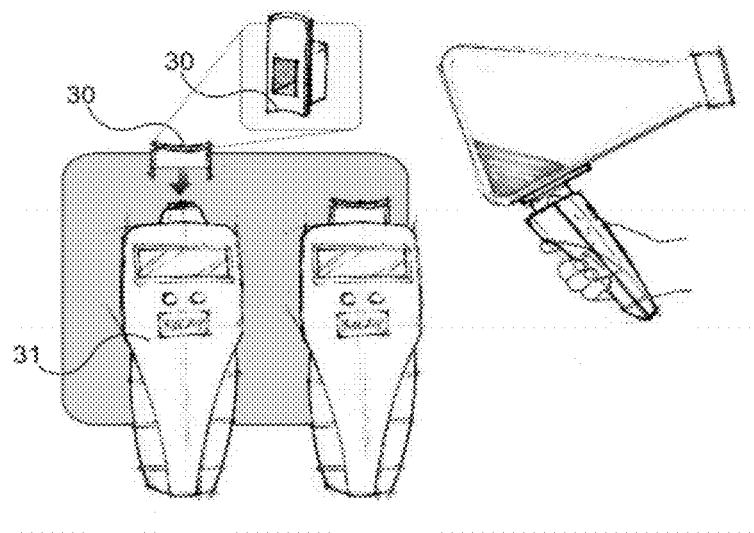
FIG. 3a-c depict device enclosures and vessel alignment guides of the present invention.
Figure 3B:
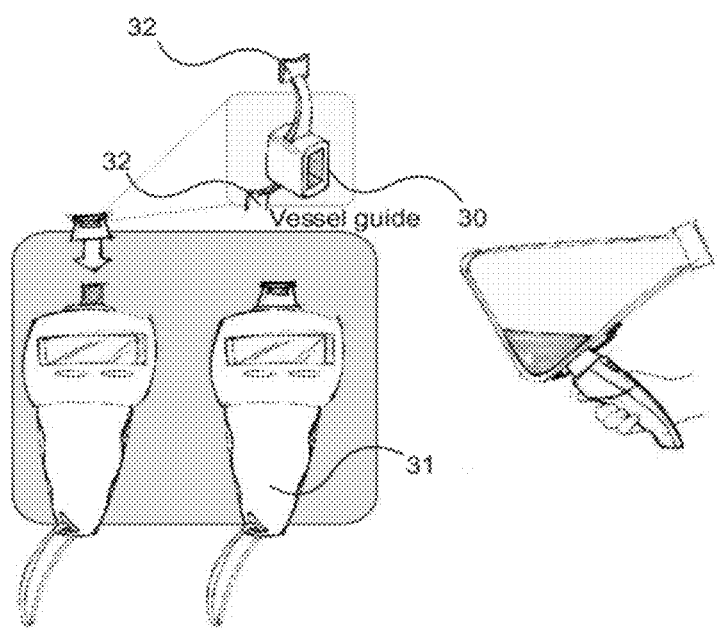
Figure 3C:
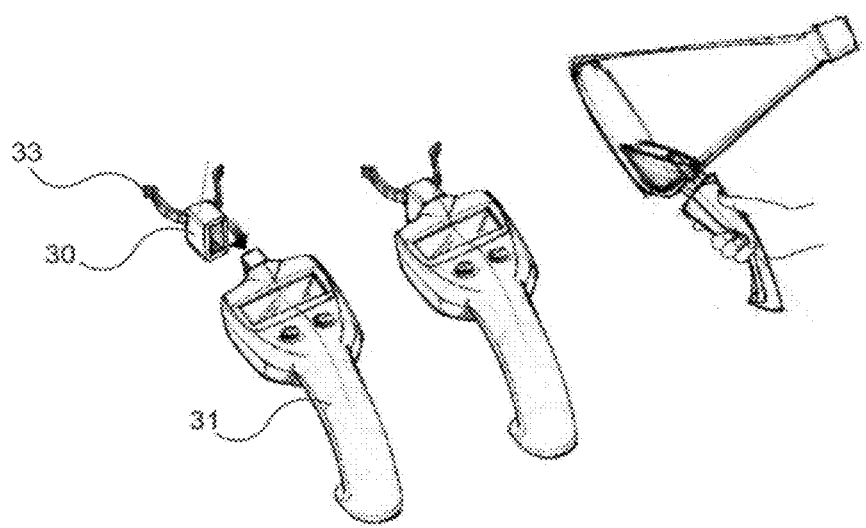

In order to assist the device operator in finding and maintaining the proper geometry required for a valid measurement, a mechanical alignment guide is provided in some embodiments of the invention. As the operator moves the sensor close to a vessel, the alignment guide partially restricts the alignment of the sensor relative to the vessel, making it easier to find and maintain the geometry in which the position switches are both simultaneously engaged. Several alignment guide embodiments are depicted in FIGS. 3a-c. In one embodiment, depicted in FIG. 3a, the alignment guide 30 is U or V-shaped in one dimension, and flat in a second dimension, to approximately match the shape of the surface of a flask or bottle to be contacted by the sensor. The alignment tool may include features that allow it to be easily removed or changed depending on the vessel type. In the guide depicted in FIG. 3a, features are provided that snap and hold the tool onto the main body of the sensor 31. The guide is removed by gently squeezing it to deform it enough to release the snap locks from the sensor body. In an alternate embodiment, channels provided in the sensor nest 41 (see FIG. 4), allow the alignment guide to slide on and off. For example, on vessels with flat windows, it may be desirable to remove the alignment guide, prior to measurement. In another embodiment the guide is held on the housing magnets. In some embodiments, the U or V-shaped feature in the alignment guide is matched to a particular vessel size. The operator could then swap out the alignment guide when using the sensor on different vessel sizes.

In another embodiment, depicted in FIG. 3b, the alignment guide includes extension arms 32 that further aid in stabilizing the positioning of the sensor relative to the vessel. In yet another embodiment, depicted in 3c, the alignment guide includes thin arms 33 that are partially deformable under force applied by the operator during alignment of the sensor with the vessel. In this manner, the guide self-adapts to a wide array of different vessel sizes, without the need to swap out the vessel guide.

Operator Feedback During Alignment and Measurement

In one embodiment, a measurement is not considered to be valid unless the proper geometry has been maintained during the entire measurement period. For this purpose, visual and/or audible feedback may be useful aids for the operator. In the embodiment depicted in FIG. 4a, both an LED indicator 43 and a speaker 42 are used to provide this feedback. In one embodiment, the LED measurement indicator has two colors, (e.g., green and red), while the speaker is capable of producing tones at multiple frequencies. When the operator simultaneously engages both position switches, a first (e.g., green) LED is turned on and flashes rapidly (e.g., at 5 Hz) and the speaker emits an audible tone (e.g., at 523 Hz). The laser is activated and signal acquisition from the detectors is activated. If the operator continues to hold the sensor in a position in which both position switches are activated for 1 second, then a second tone (e.g., at 659 Hz) is activated on the speaker, and the first measurement indicator LED continues to flash. If after 2 seconds, both position switches remain depressed, the green measurement indicator LED becomes steady (no longer flashed), and a third tone (e.g., at 783 Hz) is sounded. After an additional second, the measurement indicator LED and speaker tones are all turned off and the data acquisition is terminated. The collected data is analyzed (see the Electronics and Firmware section for details), and if the measurement is found to be valid, the first measurement indicator LED is lit up again, and all 3 speaker tones are simultaneously sounded for approximately half a second. The valid measurement is displayed on the LCD. If during the above-described measurement cycle, either of the two position switches are disengaged or the measurement is found to be invalid, all other measurement indicator LEDs are turned off and a second LED color (e.g., red) is activated, and a different (e.g., low dissonant) combination of tones (such as 240, 255, and 270 Hz) is sounded on the speaker for approximately half a second. In this manner, both audible and visual feedback, are immediately provided to the operator. Of course, many other visual and auditory indications could be used to provide feedback. The above description is provided as an example of one specific implementation, but the number of tones and colors, and/or their frequencies and wavelengths could be changed without affecting the substance of the device. In other embodiments, the audio or visual indicators are used alone.

In an alternative embodiment, the start of a measurement is triggered when both position switches are activated, but subsequent to that the reflected intensity measured by the detectors is used to determine whether the sensor position was sufficiently stable during the full measurement period. In another embodiment, data collected during unstable periods are excluded, but if a sufficient amount of data remains, a successful measurement may still be reported. In yet another embodiment, a combination of the position switch state and reflectance detector readings is used to determine whether the readings will be accepted.

Operator Interface

Figures 4A, 4B:
FIG. 4a depicts an enclosure of the present invention along with features providing an interface between the device and operator.
FIG. 4b depicts a display screen for a device of the present invention.

Beyond the measurement indicators already described above, additional methods of interfacing with the operator will provide utility in many embodiments of the invention. As depicted in FIG. 4a, such interfacing components may include: a battery charging indicator 44, button switches (e.g., Power, Base, Cal), a USB connector 45, and a display 46 for reporting measurement results and other information to the operator.

In one embodiment, the instrument is powered with rechargeable batteries. In one implementation, a battery indicator, which includes a 2-color LED (e.g. green and red), flashes a first color (e.g. green) while the battery is being charged, turns steady when the battery charging is complete, or the second (e.g. red) color is displayed if an error was encountered during battery charging.

In some embodiments, a power button is provided that allows the operator to toggle the instrument between on and off states, or to bring the instrument in and out of low-power-consumption ("sleep") modes. Additionally in some embodiments, the instrument automatically powers off or goes into sleep mode after it has been active for a certain length of time, such as 5 minutes.

In some embodiments one or more interface devices are used to allow the operator to capture and subtract a baseline value from subsequent measurements. For example, an operator may wish to collect a measurement on a flask containing only media, and subtract that measurement from subsequent measurements for which the cells are suspended in the medium. This task may be accomplished using a single button 47 (such as that labeled "Base" in FIG. 4a) as follows. After completing a measurement on a vessel containing only media, the operator presses the "Base" button within 5 seconds of the completion of the measurement. The measurement is stored electronically in the instrument as the baseline value. Subsequent measurements are automatically corrected by subtraction of this baseline value. Activation of the Baseline button outside of the 5 second window following a measurement allows the operator to toggle the baseline correction between the On and Off states, or between different stored baseline values. In one embodiment, activation of the Baseline button outside of the 5 second window following a measurement first activates a backlight on a display, and then if pressed again acts as a baseline toggle switch, as described above.

In some embodiments the operator may wish to have the ability to change the coefficients of an equation used to manipulate the reported measurement. For example, the correspondence between an off-line (e.g. spectrophotometer) measurement of OD and the reflectance measured by the device of the present invention, may depend on the size or shape of the cells or microorganisms suspended in the medium. In one embodiment, preset calibrations for particular types of organisms (e.g. *Escherichia coli, Saccharomyces cerevisiae*, etc.) are pre-programmed into the instrument and can be selected by the operator. This calibration is, in the simplest case, a linear multiplier, but may also include higher order polynomial coefficients, or other equations or transformations, as necessary to characterize the relationship between on-line and off-line OD. Methods for calibrating and converting optical reflectance measurements into particle concentrations are further described below (see "Signal Processing and Calibration") and in patent application US 2009/0075248, which is included here by reference. In the embodiment depicted in FIG. 4a, a Calibration button 48 ("Cal") is provided, that allows the operator to toggle between different calibration settings. Such calibrations may be named according to the organism and/or conditions under which the relationship between on-line and off-line OD was determined. In one embodiment, pressing the Calibration button activates a backlight on the display 49 if it is not already activated, and then subsequent button presses result in toggling of the calibration coefficients. In some embodiments, the operator is able to generate and store new calibration settings to the instrument. This may be accomplished directly through the instrument buttons, or by interfacing the device with a personal computer (PC).

In one embodiment of the present invention, the buttons, indicator LEDs, and display window 49 described above, as well as product graphics, are built into a cabled overlay, such as depicted on the left side of FIG. 4a, which plugs into the electronics board, and is attached to the enclosure, for example by an adhesive.

In some embodiments power and/or computer communication interfacing with the instrument will provide additional utility. In one embodiment both power for battery recharging and computer communication are provided through a Universal Serial Bus (USB) interface. For the purpose of battery recharging, a USB connector provided on the instrument, can be connected via a standard USB cable to either a computer having an available USB port or to an AC/DC power converter that is plugged into a standard AC power outlet and provides 5V DC through a USB connector. When plugged into a PC, USB communication between the PC and device of the present invention can be used for such tasks as: (1) updating of the device firmware, (2) downloading of data stored in the device to the PC, (3) updating of the date and/or time that is stored and/or displayed by the device, and (4) writing or modifying calibration coefficients stored in the device.

In some embodiments, a display is included on the device which is capable of providing information to the operator such as date, time, calibration setting, battery charge status, measurement number, measurement result, baseline setting, error and warning messages, and current firmware version. An example of the display after a valid measurement has been completed, is depicted in FIG. 4b. The top line shows the date and time. The second line shows the calibration setting ("*E. coli*") and battery charge status (right side). The bottom line shows the measurement number ("053"), which may be automatically incremented following each successful measurement, measurement result ("1.02"), and the baseline setting ("0.01") that was subtracted from the measurement result. For certain display types, such as liquid crystal displays (LCD), a backlight may be used to help improve the visibility of the displayed information. In order to conserve power, the LCD backlight may be dimmed or turned off after a certain period of inactivity (e.g. 5 seconds), but re-activated by events such as the reporting of a new measurement, or activation of a button. Before, during, or following measurements, the display may also be used to provide informational messages, such as error or warning messages. For example, if a measurement is reported as invalid, the display may provide a message suggesting the reason (e.g. "insufficient fluid") and/or tips remedying the error (e.g., "reposition sensor").

Sensor Housing

Figure 5A:
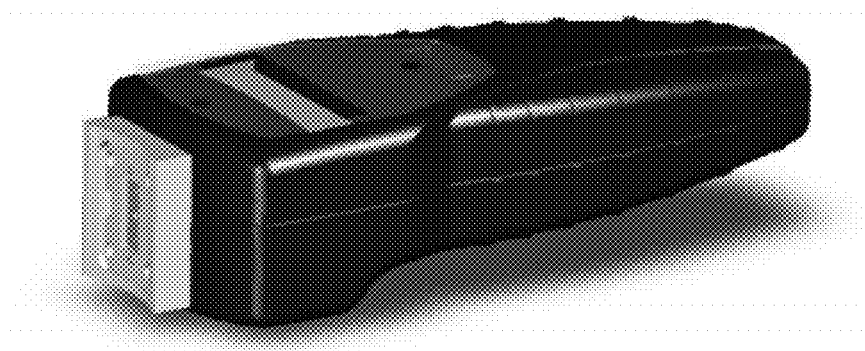
Figure 5B:
Figure 5C:
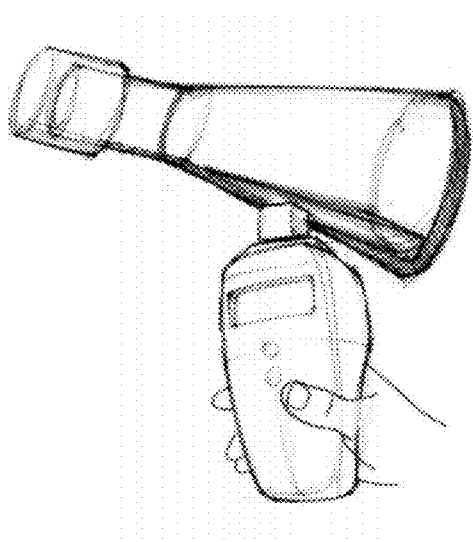

The housing for the sensor may have several additional functions beyond simply containing of all components: (1) providing easy access to interface components such as buttons, indicators, and displays, (2) protecting water-sensitive components, (3) providing a comfortable hand-grip for the operator, and (4) aiding the operator in achieving the correct orientation of the sensor relative to the vessel. Different views of one embodiment of the enclosure are illustrated in FIGS. 5a and 5b. The housing is configured so that the operator can grip the sensor with a single hand, leaving the other hand free to hold a vessel, if necessary. In addition, the buttons are placed so that they could be depressed with the thumb of the same hand used to grip the enclosure. The display screen and indicator LEDs are positioned so that the operator can see them from the same instrument orientation with which the measurement is collected. Ribs and/or a textured surface are provided in locations where the hand grips the instrument, so that even a wet and/or gloved hand may be able to securely grip the instrument and hold it against a vessel during measurement. The tapered sides of the enclosure help to accommodate many different hand sizes. The steeply curved surface on the bottom (FIG. 5b) and sides (FIG. 5a) of the enclosure, provides a convenient stopping point for the hand. This enclosure can be inexpensively manufactured as 2 parts using a mold into which plastic is injected (the parting line can be seen if FIG. 5a). In order to impede water ingress, the two halves of the enclosure may include tongue and groove features that are sealed with adhesive. Alternatively, an o-ring may be situated between the two enclosure parts, and compression force applied by screws that pull one part against the other as they are tightened. Additional means of protecting against water ingress in some embodiments include a rubber or plastic piece used to fill the cavity in which connectors, such as a USB connector, are situated. Another feature is an o-ring seal(s) in the area of the sensor head. Additionally, liquid-sensitive components, such as electrical connectors may be located in areas of the enclosure that will not lie flat against a surface, so that they would be held above the level of a small pool of accumulated liquid.

Figure 5D:
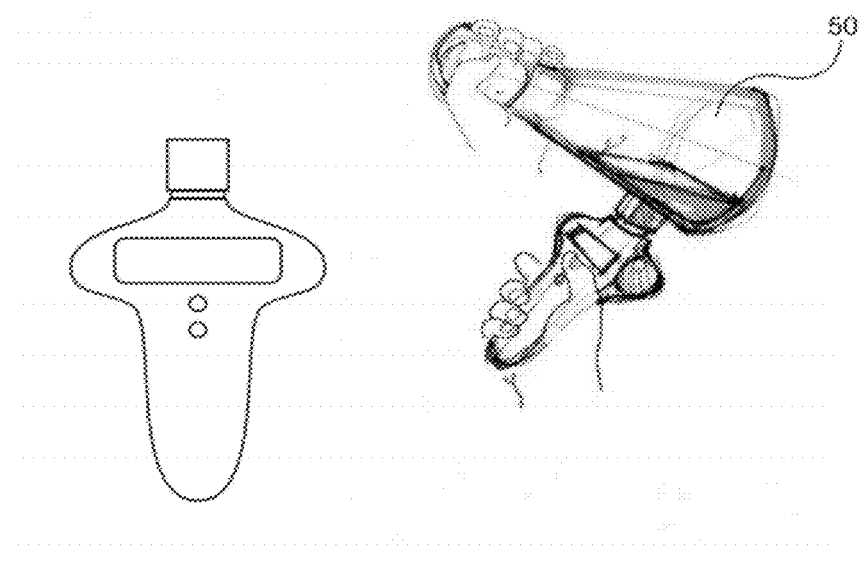
Figure 5E:
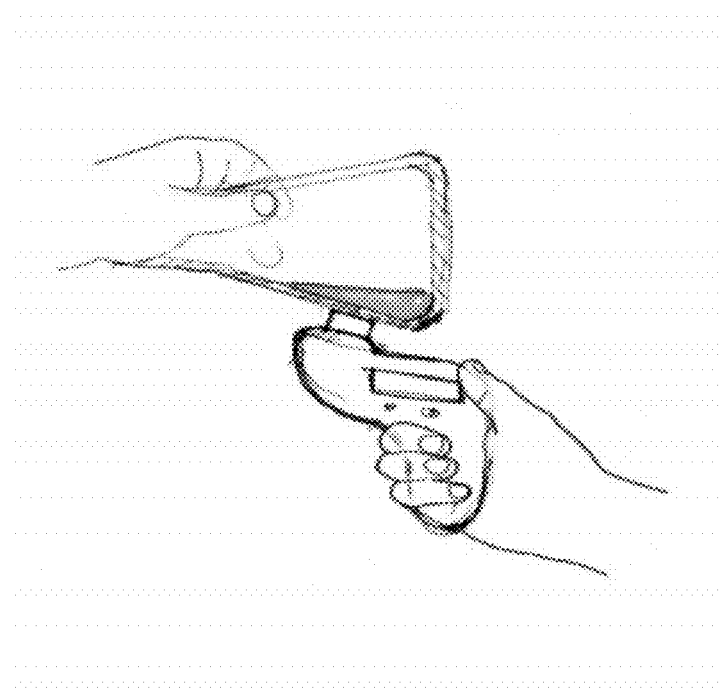
Figure 5F:
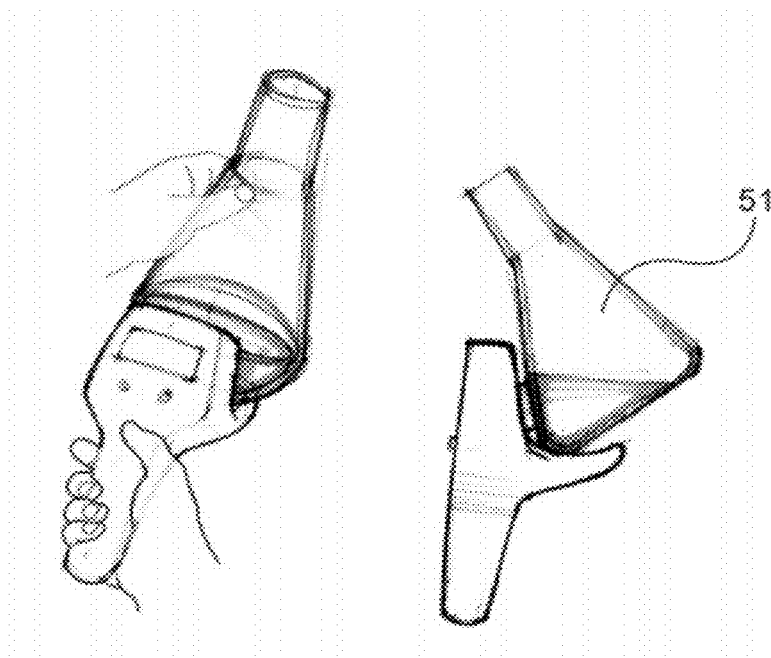

Some alternative embodiments of the enclosure are depicted in FIGS. 5c-j. The enclosure depicted in FIG. 5c has a shortened body and alternative button placement compared to that depicted in FIGS. 5a-b. In FIG. 5d, the enclosure is widened around the area of the display, which may help to guide the operator towards a particular hand grip, thereby making it easier to achieve the desired sensor orientation against a vessel (container 50). In the embodiment depicted in FIG. 5e, the sensor head is offset from the display screen, which may allow for easier viewing of the screen during a measurement. In the embodiment depicted in FIG. 5f, a support ledge is provided for resting the vessel during measurement. This feature may relieve the operator from supporting some of the weight of the vessel, and/or may aid in achieving the desired sensor-vessel orientation and/or stabilize that orientation during a measurement.

Bench-mounted (as opposed to hand-held) embodiments of the device are depicted in FIGS. 5g and 5h. In these embodiments, the weight of the vessel may be used to apply at least part of the force required to depress and activate position switches. The curved nest in the embodiment depicted in FIG. 5g, can be used to accommodate many different vessel sizes. The pre-defined angle defined by the arm and base features may be useful in automatically providing the correct amount of vessel tilt to ensure that sufficient fluid is over the sensor head during a measurement. The embodiment depicted in FIG. 5h is well suited for collecting measurements through the bottom surface of a vessel.

Embodiments that are suited for in-place measurements on vessels are depicted in FIGS. 5i and 5j. The phrase "in-place measurement" is used here to indicate that the vessel is kept in its usual position during measurement, such as in a laboratory shaker, on a shelf, etc. The long arm between the sensor head 50 and display screen 49 may allow the operator to reach between vessels in order to collect in-place measurements. The angle of the sensor head relative to the arm may predispose the instrument to having the correct orientation for measurement on a particular vessel type, such as a shake flask. The angle of the display screen relative to the arm may be adjusted to aid easy viewing of the measurement result while the sensor is still in place against a vessel during an in-place measurement.

Power Circuit

Figure 6B:
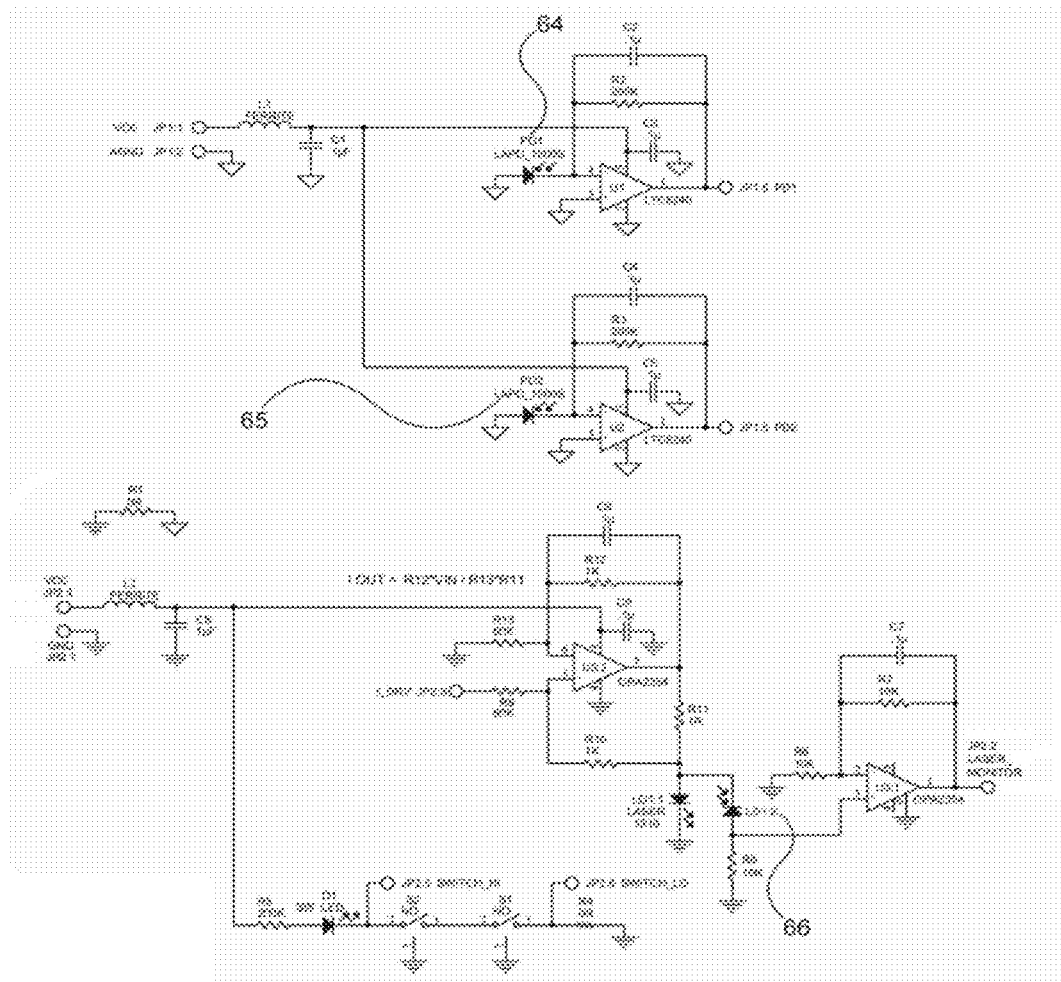
Figure 6C:
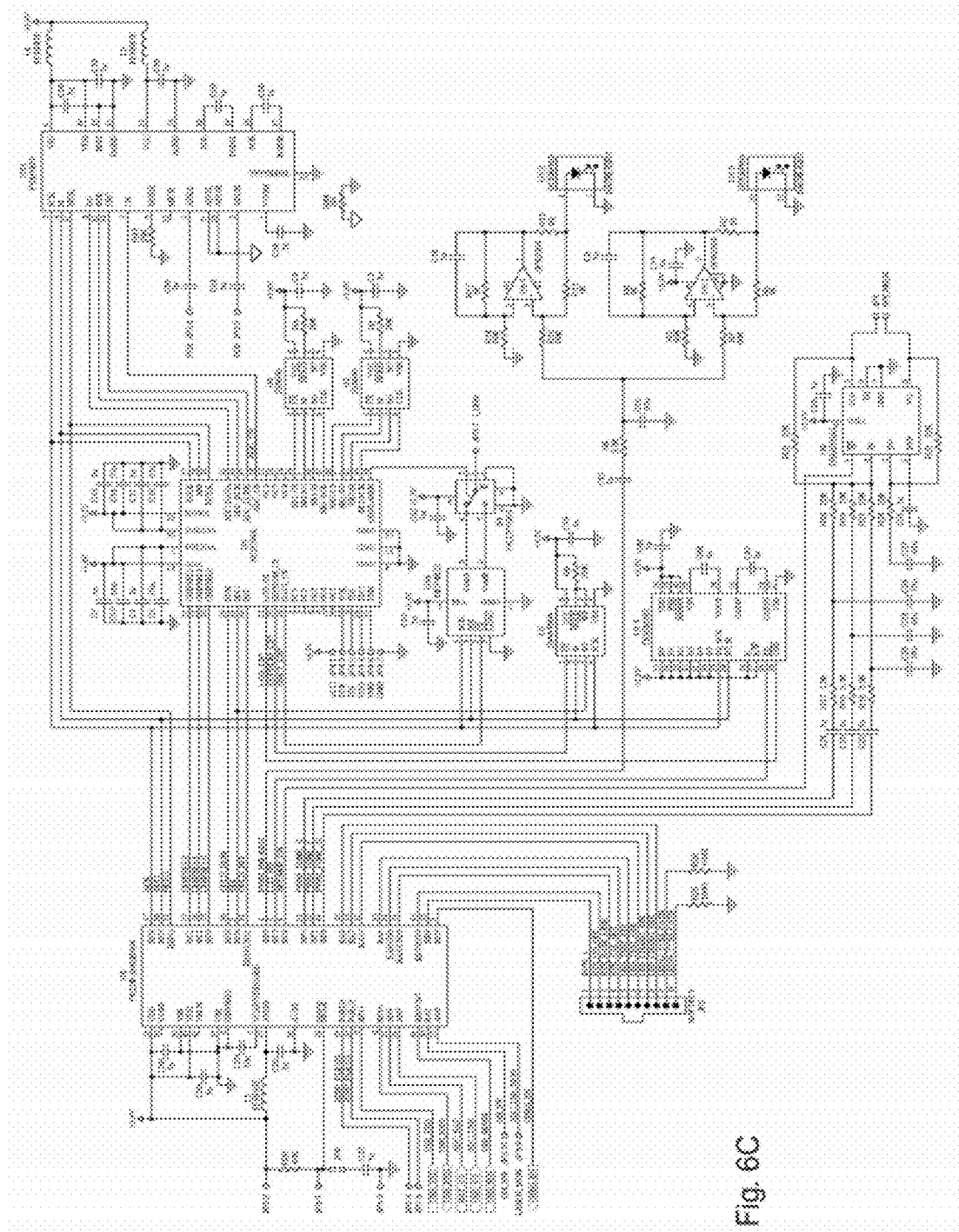

Electronic schematics for one embodiment of the present invention are provided in FIGS. 6a-c. In some embodiments of the invention, such as the benchtop versions depicted in FIGS. 5g and 5h, it may suffice to provide power for the device with a standard wall (AC) plug. However, in other embodiments, such as the hand-held embodiments depicted in FIGS. 5a-f, 5i, and 5j, it may be desirable for the instrument to operate on battery power, or some combination of battery and AC power. For those embodiments employing batteries, the use of rechargeable batteries may provide cost, convenience, and/or environmental benefits over the use of disposable batteries. An embodiment employing Low Self-Discharge Nickel Metal Hydride (LSD NiMH) batteries is further described here, although it will be understood by those skilled in the art, that many other types of rechargeable and disposable batteries could be substituted, with appropriate modifications to the electronics and firmware.

LSD NiMH batteries have the advantage of being able to hold their charge on the shelf over a time frame of years, so that they can be installed pre-charged during the manufacturing of one embodiment of the present invention. Further, the high number of recharging cycles (1000 or more) allowed by many such batteries means that the batteries can be expected to function without requiring replacement over the life of the instrument. This makes it unnecessary for the operator to have ready access to the batteries; which in turn allows simplified design of the enclosure, reduces the opportunities for moisture ingress into the instrument, and diminishes the likelihood of problems caused by an operator substituting the wrong battery type into the instrument.

FIG. 6a provides a schematic of one embodiment of a power circuit of the present invention designed to charge and draw power from two NiMH batteries 60 (BT1). Power for recharging is provided through a USB connector 61 (J1). During the charging cycle, Q1 62 and U163 cause the batteries to charge at a constant current. This current is adjustable by changing R15, but as depicted (R15=0.47 Ohms), the batteries will charge at a current of approximately 140 mA. This charging current could be raised to provide more rapid charging, but as presently set, full charging can be accomplished overnight, and the current draw is low enough so that it can easily be provided by either a USB computer port or small AC/DC wall plug-in regulator, while running little risk of damaging or over-heating the batteries through over-charging. An up-regulator (U2) is used to provide steady power at 3.3V to the rest of the electronic components in the circuit. The battery voltage ("Bat V/2") and USB voltage ("USB V/2"), as well as a digital signal indicating whether USB power is available are all monitored by a microcontroller (U15 in FIG. 6c). The microcontroller also provides a control signal (CHRG_EN) which can be used to turn on and off battery charging.

Suitable batteries for the present invention are available from numerous sources, but "Eneloop" type AA batteries manufactured by Sanyo will be used here as an example. The manufacturer specifies that these batteries have a capacity of 2000 mA-Hours (mAH), hold 75% of full charge after 3 years of storage, and can be recharged up to 1000 or more times.

In one embodiment of the present invention, battery charging is turned off after the batteries have charged for a specific period of time. For example, for batteries with 2000 mAH capacity, the circuit shown in FIG. 6a will require approximately 14 hours to achieve full charge. Therefore the microprocessor firmware could specify that full charging has been achieved if the batteries have charged for 14 hours. If the batteries still retain a partial charge at the start of the recharging cycle, the charging current is set low enough so that no damage is expected to occur to the batteries due to charging past the point of full charge. In an alternative embodiment, the charge state at the start of recharging is estimated, and this estimate is used to compute the length of the charge cycle. In still further embodiments, the voltage and/or temperature of the battery are periodically monitored, used to assess the charge state, and determine when charging is complete.

The battery voltage signal (BAT V/2) may be used directly to estimate and report the charge status of the batteries. However, more accurate determination of charge state may be accomplished by measuring the battery voltage under different states of load (as the batteries are discharged their voltage will exhibit greater depression under load). In another embodiment, the charge state of the batteries may be estimated through the known power draw of the circuit over time ("Coulomb counting").

Laser and Driver Circuit

The schematic in FIG. 6b shows a method of the present invention for converting a voltage signal (I_DRV) into a current drive for a laser (LD1:1). The voltage signal may be created by a Complex Programmable Logic Device (CPLD), such as in the circuit diagrammed in FIG. 6c. In one embodiment of the invention the laser is modulated between two current levels that are both above the lasing threshold and also within the linear range of the laser radiant flux as a function of drive current ("linear response range"). A suitable laser is, for example, Union Optronics Corp., part number U-LD-130582F. Although the lasing threshold of this laser varies with temperature, low and high laser current levels of 20 and 25 mA, respectively, will satisfy both the threshold and linearity requirements specified above, over a wide temperature range (−10 to +85 C). In an alternative embodiment, the laser threshold is determined just prior to the start of a measurement cycle. The low and high current levels are then determined relative to the current at which the laser threshold was observed, for example by adding offsets to the threshold. In one embodiment, these offsets are 5 and 15 mA, respectively, for the low and high current levels. In another embodiment, these offsets are 3 and 18 mA, respectively, for the low and high current levels. A potential advantage of varying the laser current level based on the laser threshold, is that a larger difference between the low and high currents may be achieved, while still remaining within the linear response range of the laser. A wider span of low and high laser radiant flux may allow the measurement to be collected with higher signal to noise ratio, or in a shorter period of time with equivalent signal to noise ratio.

A wide range of frequencies of the laser modulation may be suitable, but in many applications it will be desirable to avoid 50-60 Hz and its harmonics (e.g. 100-120 Hz, 200-240 Hz), since this is a common frequency of alternating current sources and may contribute noise during amplification of the detector signals. A modulation frequency of at least several hundred Hz is also desirable in many applications for reducing the contribution of other common noise sources (e.g. Johnson noise) to the measured signal. In one embodiment of the present invention a modulation of approximately 1 kHz is employed.

Detectors, Amplification, and Data Acquisition

Also provided in the schematic in FIG. 6b are circuits for trans-impedance amplification of a laser monitoring diode 66 (LD1:2), and two detectors (PD1 64 and PD2 65) used to determine the intensity of light being scattered from within a vessel. The active area of the detectors must be sensitive to light at the wavelength of the laser source. In embodiments in which the laser source emits in the range of 800 to 2500 nm, one well-suited detection material is Indium Gallium Arsenide (InGaAs). Such detectors are available from numerous sources, one example being part number LAPD-1000 sold by Chunghwa Telecommunications Corporation. These detectors have an active area approximately 1 mm in diameter, and peak sensitivity near 1300 nm. Some alternate materials for the active area of the detector include Silicon (typical wavelength range: 400-1100 nm) and Germanium (typical wavelength range: 800-1800 nm).

The detector signals generated by the circuits shown in FIG. 6b, may be further amplified and then converted to digital signals by an Analog to Digital Converter (ADC, U5), such as depicted in FIG. 6c. The ADC may also include analog and/or digital filtering of the signals in order to suppress noise at frequencies not matching the laser modulation rate. In the embodiment depicted in FIG. 6c, in addition to generating the laser modulation signal, the CPLD is also used to direct the data acquisition, so that it is synchronized with the laser modulation. The data acquisition may be performed at a higher rate than the laser modulation frequency. In one embodiment of the present invention, detector data acquisition occurs at a frequency 16 times faster than the laser modulation. Temporary storage devices, such as Static Random Access Memory (SRAM) devices (U7 and U8) may be used to collect the data as it is being acquired. By alternately writing to two or more such memory devices, continuous high-speed data collection can be accomplished. During the time that data is being written to one of the SRAM devices, data previously collected on the other SRAM device is downloaded to the microcontroller (U15), for subsequent processing.

In other embodiments, the analog to digital conversion and/or data collection are performed by a microprocessor. This may allow the circuit diagram to be simplified. On the other hand, analog to digital conversion performed within the microprocessor may be noisier than external conversion, due to the numerous other nearby signals that may be present in the microprocessor. Use of the CPLD to direct the laser modulation and data acquisition timing may also result in more precise timing, since the CPLD is purely devoted to this task, whereas the microprocessor may have many other competing timed tasks to coordinate. Use of the CPLD to control the data acquisition timing therefore may free up resources in the microprocessor, allowing it to perform other tasks more rapidly and/or efficiently.

Detector Signal Demodulation

Following digitization and transfer, the detector data are filtered and demodulated so that the resultant signals are proportional to the difference between high and low laser levels. One advantage afforded by collecting the detector signals at a substantially higher rate than the laser modulation is that it allows for reduced dependence of the derived signals on the precise phase or timing of the detector measurements relative to the laser modulation cycle. In one embodiment, for each detector type, the detector measurements collected during the low current portion of the laser cycle are summed, and subtracted from the summed detector measurements collected during the high current portion of the laser cycle. In one embodiment, the signal derived in this manner from the laser monitoring diode is used to correct the signals derived from the reflectance detector(s). In one embodiment, this correction consists of dividing the reflectance detector signal(s) by the laser monitoring signal. In this manner, the dependence of the derived reflectance signal on the laser output is reduced or eliminated.

In an alternative embodiment, the measurements collected by each reflectance detector are correlated to the measurements collected by the laser monitoring diode. This correlation may be, for example, a least squares fit to a line relating the two data sets. The slope of the line is then used as the demodulated reflectance detector signal. An advantage of this method, is that it automatically accounts for variations in the laser radiant flux. In a further embodiment, the fitting procedure is repeated after shifting the phase of one of the data sets by 90 degrees (relative to the laser modulation cycle). The two slopes resulting from this procedure are squared, summed, and the square root of the result is used as the demodulated reflectance signal. An advantage of this method ("quadrature slope correction"), is that the result will be independent of the phase of the individual detector measurements relative to the laser modulation cycle. An additional benefit of all of the demodulation methods described above is that they will compensate for sources of noise that are equally present in the low and high current phases of the laser modulation cycle. For example, light, such as ambient light, reaching a detector but that did not emanate from the laser source, may contribute to the detected signal. However, if this light is relatively invariant between the low and high laser cycles, it will be largely removed by the demodulation procedures described above.

Signal Processing and Calibration

The demodulated detector signals resulting from the above-described methods, may be further processed by digital filtering, as needed, in order to increase the signal to noise ratio of the signals. Examples of filtering methods suitable in some embodiments include band-pass, decimation, median, finite impulse response (FIR), infinite impulse response (IIR), Fourier Transform phase, and Kalman filtering.

In some embodiments, the signals are averaged over 1 or more cycles of 50 or 60 Hz. Such averaging may help to reduce the influence of noise sources, such as room lights, that contain amplitude oscillations at these frequencies. In some embodiments, signals are averaged over a time period corresponding to integral cycles of both 50 and 60 Hz; such as 5 cycles of 60 Hz and 6 cycles of 50 Hz. In this manner, the influence of noise sources oscillating at either or both 50 and 60 Hz may be effectively reduced.

In some embodiments the processed reflectance signals are offset-subtracted, where the offset term is determined during device manufacture and/or is periodically updated by measurement subsequent to manufacturing. In one embodiment, the offset term is determined by covering the sensor with a material that is highly absorbent at the laser wavelength, and measuring the detector signals. In another embodiment, the offset term is determined by pointing the sensor away from all reflective objects (e.g. into an empty space), and measuring the detector signals. In yet another embodiment, the offset term is determined by collecting a measurement on a vessel filled only with media (baseline subtraction). With or without prior offset subtraction, in some embodiments the reflectance signals are next log-transformed. The log transform may have the benefit of improving the linearity of the reflectance signal with respect to changes in particle concentration (e.g. off-line OD). In some embodiments an integrated circuit ("log amplifier") is used to log-transform the detected signal. For example, a log amplifier could replace or be used in addition to the trans-impedance amplifier circuits shown in FIG. 6b. In other embodiments, signals are processed both with and without log transformation prior to signal digitization, and the two signals are used in different particle concentration ranges. This method, implemented in Example 4, may allow particular concentration to be accurately determined over a wider range than could be accomplished by either signal alone.

In some embodiments of the invention, the reflectance signal will be transformed into a value related to particle concentration. For example, in one embodiment the signal is transformed into Optical Density (OD). The transformation into particle concentration, in some embodiments consists of a linear transformation (see Example 4, below). In other embodiments, the transformation is a higher order polynomial. In yet other embodiments, the transformation includes exponential or logarithmic terms. In still other embodiments the transformation includes an interpolation step, such as by the linear or cubic spline methods (see Example 5, below). The coefficients used in the transformation may be written into device memory during manufacturing, or written or updated after manufacturing. In some embodiments, the operator will have the option of determining and saving customized calibration coefficients into the device memory. This may be accomplished either through the direct instrument interface (e.g. buttons and display screen) provided on the instrument, or by remote interface, such as through communication between the device and a personal computer (PC).

Using the methods and devices detailed above, the time required for a measurement of particle concentration in some embodiments is three seconds or less. In other embodiments the measurement time is one second or less. As the measurement is being collected, periodic feedback regarding progress or validity, may be provided. In some embodiments, the measurement time may be variable, as determined, for example, by how long it takes to reach a desired signal to noise level.

Determining Measurement Validity

The use of position-sensitive devices for determining proper sensor-vessel alignment and measurement validity was discussed above (see the section entitled "Sensor-Vessel Alignment"). In some embodiments, reflectance detector signals are used instead of the position-sensitive devices to determine measurement validity. In other embodiments, the reflectance detector signals are used in addition to the position-sensitive devices to determine measurement validity. One embodiment employs two reflectance detectors equally spaced from the laser, such as depicted in FIGS. 1a and 1b. The signals from the two detectors are processed in the same manner and compared. One criterion for measurement validity is that the two detectors provide equivalent measurement results. Equivalence may be established, for example, if the absolute value of the difference between the two detector measurements divided by their mean is within a pre-determined range. In one embodiment, the difference between the detectors must be within 5% of their mean, in order for the measurement to be considered valid.

The advantages of the above-described methods for determining measurement validity may be better understood by considering various scenarios in which it may be desirable to declare a measurement invalid. For many embodiments of the invention, in order for the particle concentration measurement to be reproducible, a sufficient amount of medium must be present in the vicinity of the sensor head. For example, when performing measurements in shake flasks, the fluid level is often only 25% or less of the vessel capacity. Finding a suitable region for measurement on the side of the vessel may therefore be made easier by tilting the flask in the direction of the sensor. However, the operator may be uncertain whether the amount of fluid is sufficient for measurement. If the fluid level is insufficient, then it is highly likely that the amount of fluid in front of one detector will be different from that in front of the second detector. The detectors will then show a discrepancy and the measurement will be declared invalid. In a situation in which one detector is above the fluid level and one is below, the discrepancy between the two detectors will be even greater. As an example, in one embodiment of the invention, the light source is a laser emitting near 1310 nm, which will be strongly attenuated by the medium in a shake flask, but not by the air above the liquid level in the flask. The light above the fluid level will be able reflect off of the vessel walls and return to the detector, so that the detector positioned above the fluid level will collect much higher levels of reflected light than the detector positioned below the fluid level. In other situations, where both detectors are positioned above the level of the media fill level, there is also a low likelihood that a measurement will be considered valid. This is because the unimpeded reflectance of light that is seen by the detectors will be highly dependent and the orientation of the sensor relative to the vessel and the geometry of the interior of the vessel. This is particularly the case for shake flasks which have an inherent tapered shape, which makes the reflectance cavity seen by detectors at two different positions above the liquid level very unlikely to match.

Measurement Timing for Agitated Fluids

In some embodiments of the invention, the particle concentration in the medium is measured while the vessel is being agitated. In such situations, there may be time periods when there is an insufficient amount of fluid in front of the sensor in order to make an accurate determination of particle concentration, while at other times there is sufficient fluid. In such embodiments, the measurement is collected rapidly enough so that multiple measurements are performed within each agitation cycle. In some embodiments, data collected during time periods when insufficient fluid is present in front of the sensor are excluded during the data processing stage. Methods for determining when sufficient fluid is in front of the sensor have already been described above, and include, for example the use of one or more capacitance sensors and/or optical detectors.

In other embodiments, the sensor is intentionally situated so that as the vessel is agitated, measurements are collected both with no fluid in front of the sensor at certain times, and with substantial amounts of fluid in front of the sensor at other times. The measurements collected in the two time periods are combined during the data processing step. For example, in one such embodiment a ratio is computed of the signal measured with substantial fluid present in front of the sensor (I), to the signal measured when fluid is absent (I0). In some embodiments, the logarithm of this ratio is further computed and related to particle concentration. Some potential advantages of embodiments employing such ratiometric methods include: (1) The sensitivity of the resultant measurement to changes in source irradiance, detector sensitivity, and optical coupling efficiency between the sensor and vessel may be reduced or eliminated, (2) The influence of stationary objects in the optical path may be reduced or compensated for, (3) The sensor may constructed from low-cost parts that are suitable for a low-cost or disposable application.

Verification, Correction, and Calibration of Sensor Performance

In some embodiments of the invention, a material with a stable reflectance is provided for the purpose of checking, and if necessary correcting, the sensor performance. Examples of suitable materials for this purpose are Kynar and Teflon. The expected reading may be stored in instrument memory or written on the standard itself. If the actual sensor reading does not agree with the expected reading, in one embodiment correction factors are applied to the reflectance measurement to bring it back into agreement. These correction factors may then be stored and applied to subsequent readings.

For the purpose of sensor calibration during instrument manufacture at least one or a series of several materials providing a gradation of different reflectance values may be provided. An example of a suitable material for providing such a variable reflectance signal is acrylic with variable amounts of a scattering substance, such as titanium oxide, mixed in prior to polymerization.

Combined Sensor and Barcode Scanner

In some embodiments of the present invention, a barcode scanner is included. Bar codes are provided, such as on adhesive stickers, that can be conveniently situated on vessels, such as shake flasks. The barcode scanner may be provided as a separate portion of the instrument, or may be incorporated into the sensor head used to measure the particle concentration in vessels. The barcode scanning capability provides a convenient way of tracking the concentration measurements made across multiple vessels. So, for example, when the particle concentration measurement is stored in instrument memory, the barcode reading of the vessel is also stored and associated with the particle concentration measurement. In one embodiment, a particle concentration measurement and a barcode reading are performed sequentially, and thereby associated with each other. In one such embodiment, the particle concentration measurement is performed first, and once a successful measurement has been collected, the operator is prompted to position the device over the bar code for reading.

Wireless Data Transmission

In some embodiments of the invention, wireless transmission of data from the sensor to an ancillary or peripheral device is provided. Examples of such ancillary or peripheral devices include a personal computer, handheld communications device, portable memory device, CPLD, microprocessor, and microcomputer. Transfer of data from the sensor to ancillary device may occur automatically each time a successful measurement is completed. Alternatively, data may be transferred in response to a prompt provided by the operator (such as a button on the sensor enclosure that is depressed). Combination of the wireless data transmission and bar code scanning capability provide a particularly convenient method of tracking and storing the particle concentration measurements, in some embodiments of the present invention.

In one embodiment of the invention, wireless data transfer capability is provided as an optional feature that is enabled, for example, by plugging a wireless data transfer device into a USB port on the device. In another embodiment of the invention, a significant amount of the processing of the sensor signal occurs in a device that is peripheral to the sensor, to which the sensor data has been wirelessly transferred. This embodiment may be particularly well suited to applications where the sensor is disposable, such as when used in conjunction with a disposable bioreactor.

PC Software

Although many embodiments of the present invention are primarily used as stand-alone devices, communication with an ancillary device such as a personal computer (PC), will provide useful additional features, in some embodiments. In the schematic shown in FIG. 6a, a USB serial interface integrated circuit (U10) is used to enable communication between a microprocessor in the device and a personal computer. U10 enables two-way serial communications through a virtual communications port (VCP). In some embodiments of the present invention, a software program is provided that can be loaded onto a PC, enabling such functions as: (1) downloading of data from device to PC, (2) updating of the device date and time, and (3) generation and uploading of calibration coefficients from PC to device.

Patch Sensor

In another alternative embodiment of the invention, certain components of the sensor are built into a housing that can be affixed to a vessel, thereafter providing the capability of making multiple measurements without the need for reapplication of the sensor to the vessel. In one such embodiment, a light source and detector are built into an adhesive patch that is applied to a vessel. The construction and example measurements collected with one such embodiment are described in Example 5. Examples of vessels to which such a sensor may be applied include disposable bioreactors, shake flasks, fermentors, bioreactors, and miniature fermentors and bioreactors. In some embodiments a detector pre-amplifier is also included within the patch. In some embodiments this patch is designed to be disposable. The housing is connected through a cable or wireless interface to a controller circuit that processes the detector signals and reports the particle concentration to the operator. In another embodiment the housing contains fiber optical components which relay the light source and/or detector optical signals between the housing and a separate controller.

Multiplexed Sensor

Figure 11:
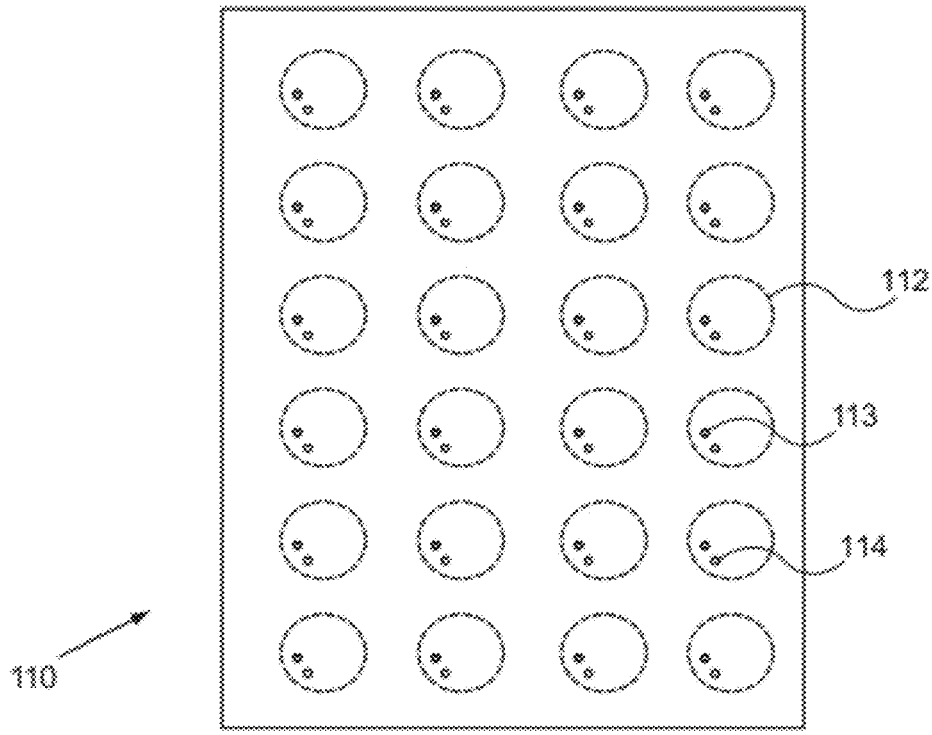
FIG. 11 depicts an arrangement of source-detector pairs beneath a multi-well plate allowing for simultaneous monitoring for particle concentration in multiple wells.

In some embodiments, multiple sensors are interfaced into the same controller circuit, from which measurements from the different sensors may be reported to the operator. An example embodiment for measuring particle concentrations in a 24-well plate 110 is depicted in FIG. 11. The plate outline is depicted from below, with the approximate inner diameter of each well 112 depicted by dashed lines. Beneath each well a source 113-detector 114 pair is placed near the edge of the well. Placement of the source-detector pair near the edge of the well may allow the measurement to be made accurately even when the plate is being agitated at high speeds, such as may result in a deep vortex at the center of each well. In one embodiment, fiber optics are terminated at each well, and coupled to source and detectors at the opposite end of the fiber. Each fiber optic may be coupled to a single electro-optical element (source or detector), or a fiber splitter or switcher may be used to multiplex the electro-optical elements between multiple fibers. In one particular embodiment, the source-detector separation is in the range of 0.5 to 5 mm. In some embodiments fiber optics with core diameter in the range of 100-300 mm are selected. One advantage of using fiber optics is they inherently limit the optical divergence or acceptance angle, as determined by the numerical aperture of the fiber. In one embodiment, the numerical aperture of the fiber is selected to be about 0.2.

In an alternative embodiment, only one fiber optic is used in each well. The source is coupled into the same fiber as is used to collect the scattered light. In some embodiments the polarization of the source and detection arms is crossed so as to discriminate against specular (surface) reflections, in favor of diffuse scattering, emanating from within the medium.

In yet another embodiment, multiple source-detector pairs are used in each well, so as to extend the linear range of the combined sensor response to changes in particle concentration.

Alternative Embodiments

In some embodiments, the position of the laser(s) and detector(s) may be interchanged with each other while still maintaining the essential sensor functionality. For example, in the embodiment depicted in FIG. 1a, the laser could be replaced with a detector, and the detectors replaced by two lasers, as shown in FIG. 1d. In order to separately measure the reflectance that originated with each laser, the lasers may be turned on at different times, or be modulated at different frequencies. When determining measurement validity, the detected signals due to the two different sources are compared, in an equivalent fashion to the manner in which the two detected signals emanating from the single source are compared when employed the sensor depicted in FIG. 1a.

In other embodiments, a radial arrangement of detectors, such as depicted if FIG. 1f, surrounds the laser. The constraints on the sensor-vessel geometry required for a valid measurement of particle concentration are lessened by using the signals from all source-detector pairs. In one such embodiment, the source-detector pairs positioned opposite each other in the ring are compared, and the two pairs matching each other most closely are selected for the particle concentration measurement. In some embodiments, position sensors are also used, but the number of required position sensors is reduced by the radial source-detector arrangement. For example, a single position detector positioned near to the laser is provided in the embodiment depicted in FIG. 1f. In one such embodiment, the laser and/or detectors positions represent the end face of fiber optics which are connected to the electro-optical components (laser and detectors) at the opposite end of the fiber optic (not shown). In other such embodiments, the laser and detector positions are swapped, so that a radial arrangement of lasers surrounds a detector.

In other embodiments, additional lasers and/or detectors are added so that there are source-detector pairs at multiple separation distances. One such embodiment is depicted in FIG. 1e. Detectors 10 and 11 may be employed in a manner similar to the embodiments described in reference to FIG. 1a. Detector 14 may be used to extend the linear range response to particle concentration. Optimal combinations of source-detector distances for achieving wide linear response to particle concentration, and algorithms for combining the signals from the different source-detector pairs are described in Patent Application US 20090075248, which is included here by reference.

In some embodiments the laser modulation is varied according to the size of the measured reflectance signal detected from the sample. In one such embodiment, the amplitude of the laser modulation ("modulation depth") is increased until a desired reflectance value has been obtained, or a maximum modulation depth has been reached. In this manner the dynamic range of the measurement may be extended, for example allowing a wider range of particle concentrations to be accurately determined.

In some embodiments an analog band-pass filter is added to the detector amplification electronics, that selectively amplifies signals at the frequency of the laser modulation, while attenuating signals outside of the bandpass range.

In some embodiments the reflectance signal is log-transformed twice and related to a singly log-transformed quantity related to particle concentration, such as optical density. This relation may be a linear transformation, higher order polynomial transformation, or other transformation, such as described above. One advantage of some such embodiments is that the relationship between the twice log-transformed reflectance signal to the singly log-transformed particle concentration is linear over a wide range of particle concentrations. After the linear transformation, the signal is inverse log transformed, in order to be representative of particle concentration.

In some embodiments a measurement of signal stability, such as a standard deviation computed across repeated measurements of the signal, is used as a method of qualifying signals as being sufficiently accurate for further processing into an estimate of particle concentration. In one embodiment, if the standard deviation exceeds a pre-defined threshold, the user is informed that the measurement was too unstable to provide an accurate prediction of particle concentration. Instructions for remedying this fault may also be provided through the user interface.

In many of the embodiments described above, a light source emitting in the vicinity of 1310 nm is described. However, light sources emitting in many other spectral regions will also be suitable in the present invention. The absorbance spectrum of water contains multiple bands in the near infrared spectral region, with generally increasing absorbance peaks with increasing wavelength. The spectral region may be selected according to the desired source-detector separation, with suitable spectral regions generally increasing in wavelength as the source-detector separation is decreased. For example, in applications requiring a source-detector separation in the range of 1-10 cm, the 900-1150 nm spectral region is well suited. Water absorbance in this region ranges between about 0.06 and 1.0 cm$^{-1}$, corresponding to a range of mean absorbance path lengths from 1 to 16 cm. One advantage of working in this spectral region is that numerous commercial sources are available, and inexpensive low-noise detectors with Silicon active areas may be employed. In another alternative embodiment, a source in the vicinity of 1550 nm is employed. Such sources have been extensively developed within the telecommunications industry. The strong water absorbance in this spectral region (12 cm$^{-1}$), makes it well suited for short source-detector separations, such as in the mm and sub-mm range, particularly about 1 mm. In a further embodiment of the invention, source-detector pairs at multiple separation distances are employed in the same sensor, with each source wavelength selected so that the mean path length for water absorbance is roughly matched with the separation distance (e.g., within a factor of 10).

In many invention embodiments described herein, the physical separation and orientation between sources and detectors are used to diminish the influence of surface (specular) reflections on the measurement in favor of diffuse reflections from particles within a medium. In other embodiments of the invention, additional or alternative methods are used for reducing the influence of specular reflections. Examples of such methods include: (1) the use of crossed-polarizers, (2) Angling of the source and/or detectors, (3) high frequency (e.g. GHz) modulation and detection, (4) the use of short light pulses and high speed detection, and (5) photo-acoustic measurement, where an acoustic detector is used to detect and depth-resolve a light pulse.

In the description of some embodiments, a laser diode light source is described. However, many other light sources could be substituted for the laser diode without substantially modifying the essential features of the invention including: vertical cavity surface emitting lasers (VCSELs), light emitting diodes (LEDs), resonant cavity light emitting diodes, solid state lasers (e.g. Nd-YAG), and gas lasers (e.g. HeNe).

Example 1

Particulate Reader with a Single Light Source-Detector Pair

Figure 1C:
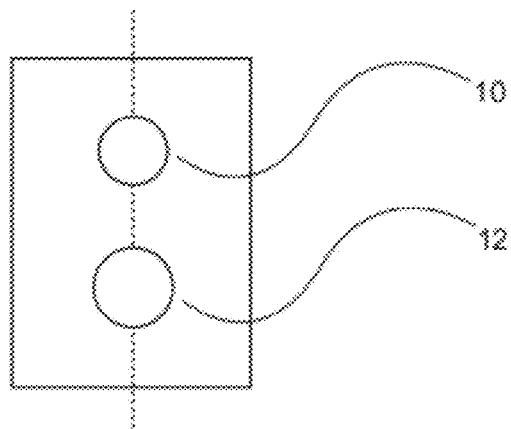
Figure 1D:
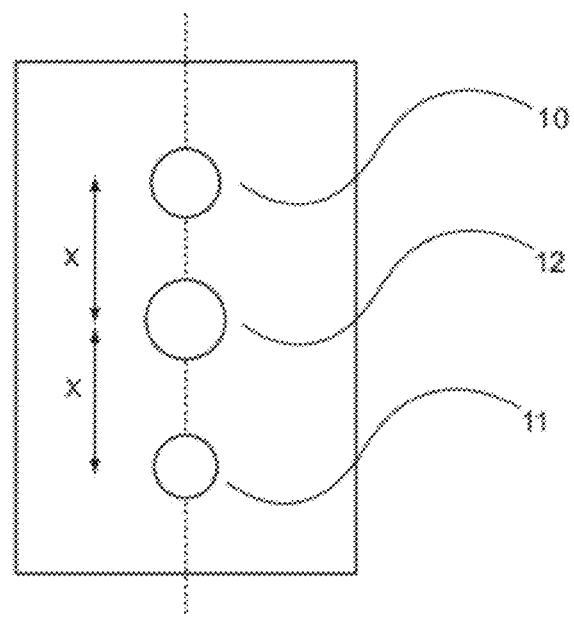
Figure 1E:
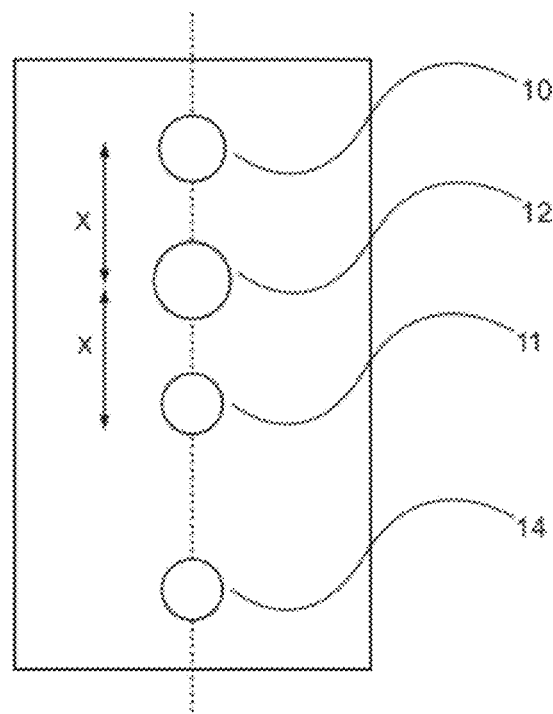
Figure 1F:
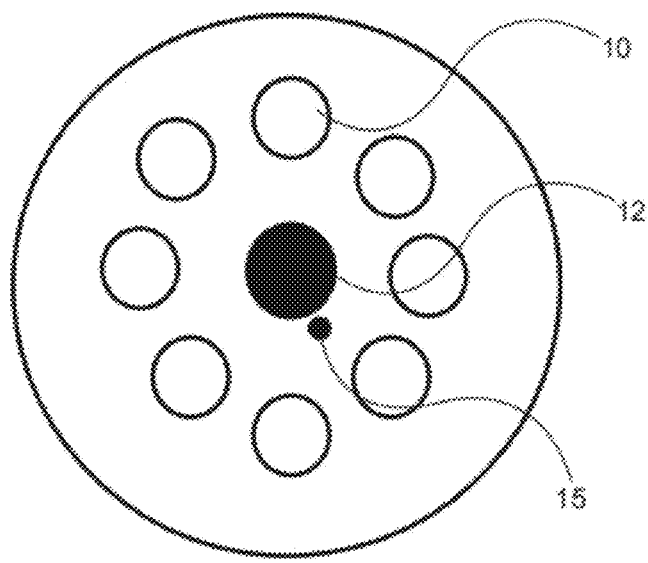
Figure 2A:
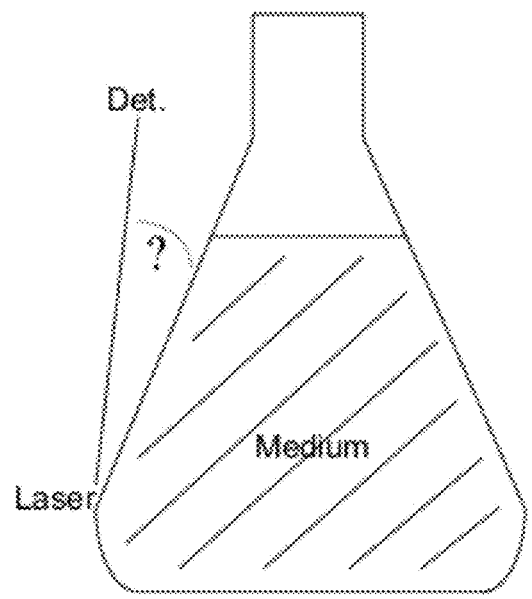
FIGS. 2a-d define angles (q, γ, and f) and position (d) of a sensor of the present invention relative to a vessel whose contents are to be measured.
Figure 2B:
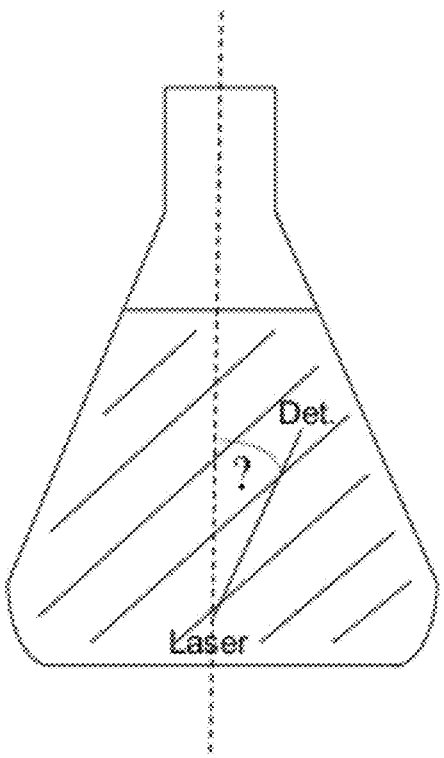
Figure 2C:
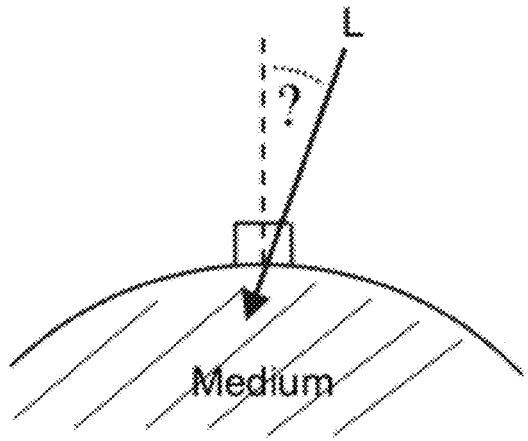
Figure 2D:
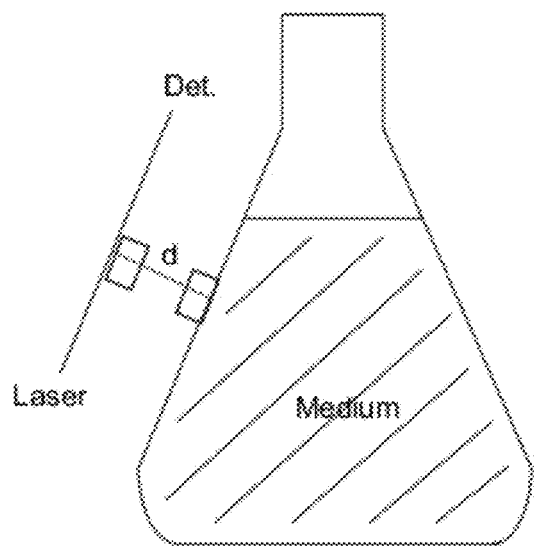

Using a device such as depicted in FIG. 1c, the sensitivity of reflected intensity to the geometrical relationship between the sensor and vessel was experimentally characterized. The vessel was a 250 mL PET shake flask (VWR part number 89078-222), partially filled with 6.4 g/L Baker's yeast (Red Star Active Dry Yeast) suspended in 0.9% aqueous NaCl. The light source was a diode laser (Roithner Lasertechnik, part number S1300-5MG-FW) with 1310 nm center wavelength, 3 nm spectral half-width, approximately 9 degree divergence angle, and 5 mW radiant flux, driven with a 1.6 kHz sinusoidal current wave with a peak-to-peak amplitude of 20 mA. The detector (Chunghwa Telecom., part number LAPD-1000) had a 1 mm InGaAs active area, which after transimpedance pre-amplification was further amplified in phase with the laser modulation frequency, using a lock-in amplifier (Stanford Research Systems, SRS510). The optical components were glued into a housing machined from black 20% glass-filled polycarbonate. The optical axes of the laser and detector were positioned parallel to each other and spaced 6 mm apart (center-to-center). The detector was placed behind an aperture 1.6 mm in diameter and 5 mm deep, thus limiting the acceptance angle to approximately 18 degrees.

The sensor was mounted to the vessel in a generally vertical orientation (with the long axis of the sensor parallel to the flat surface of the vessel), and the effect of rotating the sensor-vessel angles $\theta$ and $\phi$ (as defined in FIGS. 2a and 2c) on the detected reflectance intensity was measured. The results, summarized in Tables 2 and 3, show that the reflectance intensity is much more sensitive to changes in $\phi$ than $\theta$. For example, in order to maintain the change in reflectance intensity at less than 5%, $\phi$ should be limited to 5 degree deviations from zero, whereas deviations in $\theta$ of nearly 25 degrees can be tolerated. In the embodiment of the present invention depicted in FIG. 1a, the location of the position switches is such that simultaneous activation of the switches is possible over a narrower range of rotation in $\phi$ than $\theta$. This feature of the invention aids the operator in achieving accurate reflectance measurement without making the angular tolerance overly restrictive, such as might make it difficult to achieve or maintain the desired orientation during the measurement.

TABLE 2

Dependence of Reflectance Intensity on $\theta$.

| $\theta$ (degrees) | % Change in intensity |
| --- | --- |
| 0 | — |
| 25 | 6.3 |

TABLE 3

Dependence of Reflectance Intensity on $\phi$.

| $\phi$ (degrees) | % Change in Intensity |
| --- | --- |
| 0 | — |
| 5.3 | 5.2 |
| 10.6 | 11.1 |

Next, the angles $\phi$ and $\theta$ were held fixed while varying the orientation angle of the long axis of the sensor relative to flat dimension of the vessel (g as defined in FIG. 2b), and measuring the effect on the reflectance intensity. The results, summarized in Table 4, show that the reflectance intensity is only weakly dependent of g. Nevertheless, if highly accurate reflectance measurements are desired (e.g., in order to maintain <5% error), some restriction in $\gamma$ may provide benefit. The U or V-shaped features in the alignment guide provided in some embodiments of the present invention (e.g. FIGS. 3a-c), will automatically guide the operator towards positioning the sensor so that $\gamma$ is close to zero, and may help prevent the position switches from being simultaneously switched when $\gamma$ deviates too far from zero.

TABLE 4

Dependence of Reflectance Intensity on $\gamma$.

| $\gamma$ (degrees) | % Change in Intensity |
| --- | --- |
| 0 | — |
| 90 | 8.8 |

Next, the angles $\phi$, $\theta$, and $\gamma$ were held fixed (at zero) while varying the distance between the sensor and vessel, d (as defined in FIG. 2d), and measuring the effect on the reflectance intensity. The results, summarized in Table 5, indicate that translational variations of up to nearly 2 mm may be tolerated while still maintaining less than 5% change in reflectance intensity. Through the use of position switches, included in some embodiments of the present invention, this positional tolerance is readily maintained.

TABLE 5

Dependence of Reflectance Intensity on d.

| d (mm) | % Change in Intensity |
|---|---|
| 0 | — |
| 0.5 | 0.5% |
| 1.0 | 2.5% |
| 1.5 | 3.5% |
| 2.0 | 6.7% |
| 3.0 | 13.6% |

The effect of varying d was re-measured after replacing the yeast solution in the vessel with water. Assuming that the signal measured on the blank vessel is entirely due to surface reflections, the percent contribution of these reflections to the signal measured on a vessel containing 6.4 g/L yeast was computed and is shown in Table 6. Surface reflections made no significant contribution to the signal when the separation between the sensor and vessel was maintained at 2.0 mm or less. This result shows the effectiveness of the apertures and restricted divergence and acceptance angles of the present invention at preventing contributions of surface reflections to the measured signal, as long as the distance between the sensor and vessel is properly controlled during the measurement.

TABLE 6

Effect of Surface Reflections on Measured Intensity.

| d (mm) | % Change in Intensity |
|---|---|
| 0 | 0.0% |
| 0.5 | 0.0% |
| 1.0 | 0.0% |
| 1.5 | 0.0% |
| 2.0 | 0.0% |
| 3.0 | 1.6% |
| 4.0 | 10.6% |
| 5.0 | 19.2% |

Example 2

Determinations Through Various Containers

The effect of vessel type on device measurement accuracy was tested for one embodiment of the present invention. The device and measurement conditions were as described in Example 1, except that the yeast solution was transferred into various different vessel types for measurement, and the sensor-vessel geometry was fixed, as described in Table 1. The vessel types that were tested included 3 different materials; polyethylene terephthalate (PET), polycarbonate (PC), and glass; with vessel wall thicknesses ranging between 1.8 and 3.9 mm. The measurement error was found to be less than or equal to 5% in all cases, as summarized in Table 7.

TABLE 7

Experimental measurements of OD on different vessel types.

| Vessel Type | Wall Thickness (mm) | Wall n | Error |
|---|---|---|---|
| 250 mL PET shake flask | 1.8 | 1.57 | −5.0% |
| 250 mL glass shake flask | ~2 | 1.52 | 1.2% |
| 500 mL round glass | 3.3 | 1.52 | +5.0% |
| mini-fermentor 1000 mL PC round bottle | ~2 | 1.58 | −2.6% |
| 2000 mL glass shake flask | 3.9 | 1.52 | 1.2% |

In order to systematically test the effect of wall thickness on the measurement accuracy, a square glass vessel was constructed with walls having four different thicknesses of glass, ranging from 3.1 to 5.6 mm. By moving the sensor between the four walls of the vessel, the effect of glass thickness was tested. As can be seen in Table 8, no clear relationship was found between wall thickness and measurement error. In all cases the measurement error was less than 5%.

TABLE 8

Measurement of OD as a function of wall thickness.

| Wall Thickness (mm) | Error |
|---|---|
| 3.1 | 2.8% |
| 3.9 | −4.7% |
| 4.8 | −1.4% |
| 5.6 | 0.5% |

Example 3

Effect of Media Depth

The effect of fluid depth on the reflectance measurement accuracy was tested by placing a PET bottle on its side, measuring reflectance through the bottom side of the vessel, and varying the amount of yeast solution in the container. The solution contained 16 g/L Baker's yeast (Red Star Active Dry Yeast) suspended in 0.9% aqueous NaCl. The sensor was as described in Example 1. The sensor-vessel geometry was restricted as described in Table 1. As shown in Table 9, the fluid depth above the sensor was decreased from 56 to 10 mm with only a 2% change in the reflectance intensity. This example demonstrates one of the advantages conferred by the present invention: by using a light source with emission that is strongly absorbed by the medium, only a shallow depth of fluid (e.g. 1 cm) is needed in order to accurately measure the reflectance intensity.

TABLE 9

Reflectance as a Function of Fluid Depth

| Fluid Depth (mm) | % Change in Intensity |
|---|---|
| 56 | — |
| 33 | 1.3% |
| 18 | −1.5% |
| 10 | −2.3% |

Example 4

Correlation of Scatter and OD

An example of a transformation of a measured reflectance signal into Optical Density units is next described. The sensor was as described in Example 1. The detector amplification circuit and digital conversion method were also similar to that described in Example 1, except a logarithmic amplifier (Analog Device AD8310) was added between the pre-amplifier and lock-in amplifier. Signals both with ("log signal") and without ("linear signal") logarithmic amplification were further amplified, demodulated, and digitized by lock-in amplifiers. Yeast solutions in 0.9% NaCl were prepared over a range of concentrations from 0.0032 to 16 g/L. Yeast concentrations were converted into "OD (600)" by multiplying the yeast concentrations by a factor of 3. This conversion factor was experimentally determined using a laboratory spectrophotometer (Perkin Elmer, model lambda 9), but when tested on some other commercially available spectrophotometers, was found to be somewhat dependent on the particular model of spectrophotometer that was used. When measuring scattering rather than strict absorption, the optical arrangement in a spectrophotometer may affect the extent of measured scattering. Variations in such aspects as the illumination beam or detector acceptance angle between different spectrophotometer models may therefore change the measured OD.

Figure 7A:
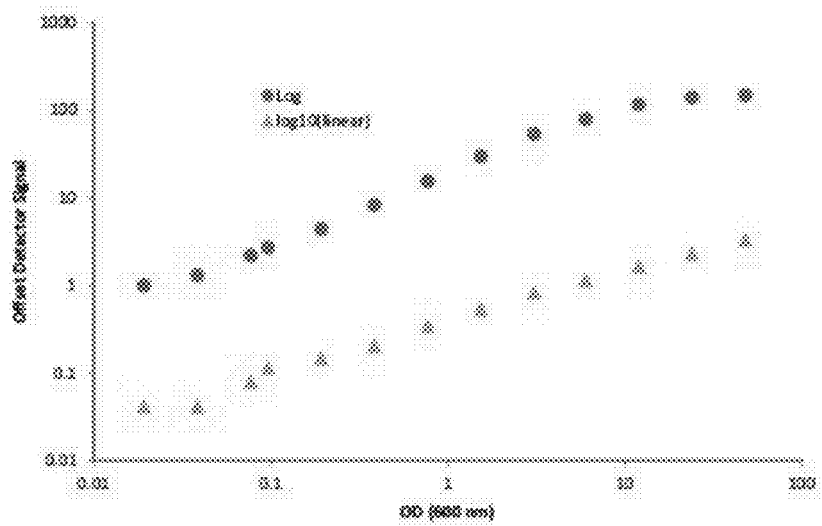
FIGS. 7a-b are graphs of the processed reflectance signals vs. OD(600) generated by a device of the present invention.
Figure 7B:
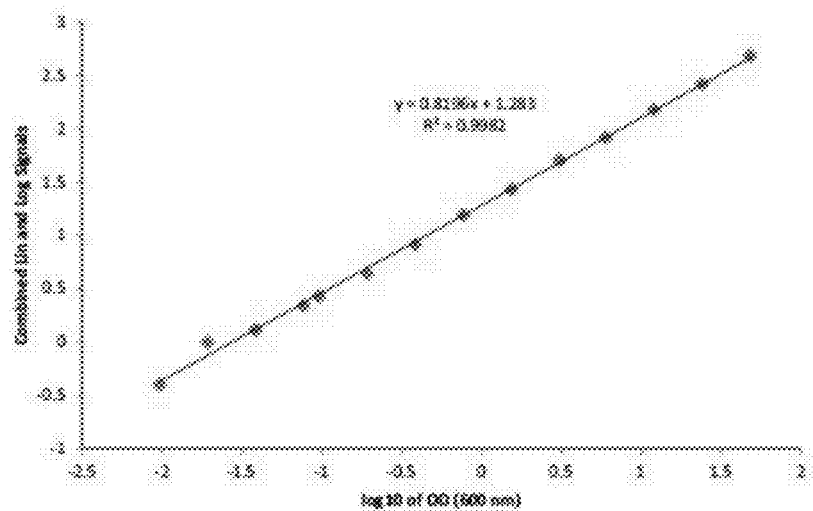

The linear signal, after demodulation and digitization by the lock-in amplifier was offset-subtracted and then log-transformed. The same offset was applied to at all yeast concentrations; and the offset was selected to maximize the linearity between the resultant signal and OD(600). The resultant linear signal is shown overlaid with the log signal in FIG. 7a. Either the linear or log signal alone could be transformed into OD(600), using methods described above (see section "Signal Processing and Calibration"). However, by combining the two signals, an even wider linear range of response with OD(600) may be possible. For this purpose, the linear signal was further offset, log transformed again, and scaled to match the additionally log-transformed log signal. The region between about OD 0.7 and 12 was used to determine the scaling and offset terms for further linearly transforming the linear signal to match the log signal. Then by using the log signal in the low OD range (e.g. OD<1) and the linear signal in the high OD range (OD>1), linear response to OD could be attained over a range of ODs from approximately 0.01 to 50, as shown in FIG. 7b. The matching of the linear signal to the log signal could also be performed without the second log transform step. Methods for achieving a smooth transition between 2 reflectance signals are further described in patent application 20090075248, the full text of which is incorporated here by reference.

Example 5

Self Adhesive Sensor

Figure 8:
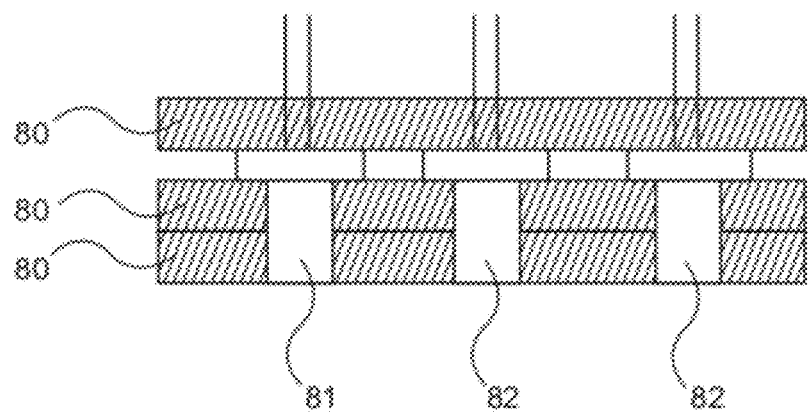
FIG. 8 depicts a sensor of the present invention, constructed from a low-cost adhesive material.

The construction and example measurements collected with a low-cost adhesive sensor are next described. This type of sensor may be useful for applications where a disposable sensor is desired, such as for use on a disposable bioreactor. The "enclosure" or substrate material for the sensor consisted of 3 layers 80 of 1.8 mm thick double-sided flexible adhesive tape (3M product number 2-0300), with holes punched through 2 of the layers to surround the diameter of the source 81 and detectors 82 (see FIG. 8). The third adhesive layer was used to support the rear of the optical components and was also used as a feed-through for their wire leads. The light source (Hamamatsu part number 210822) was an un-lensed Light Emitting Diode (LED) with center wavelength of 1300 nm, spectral half width of 90 nm, and radiant flux of 3.4 mW at 50 mA drive current. The detectors (Advanced Photonix part number SD 012-11-41-211) employed an un-lensed 0.3 mm diameter InGaAs active area. The center-to-center distance from the LED to detector 1 was 8.0 mm, and to detector 2 was 20.5 mm. The LED was directly driven through a 250 Ohm resistor by a multi-function generator (Tektronix FG507) with a 12.5 V peak sine wave at a modulation frequency of 1 kHz. Each detector was wired to the current input port of a lock-in amplifier (Stanford Research model SR510). Thus, in this embodiment, the sensor portion consisted of only the LED, detector(s), and adhesive tape; all other components were located peripherally.

Figure 9:
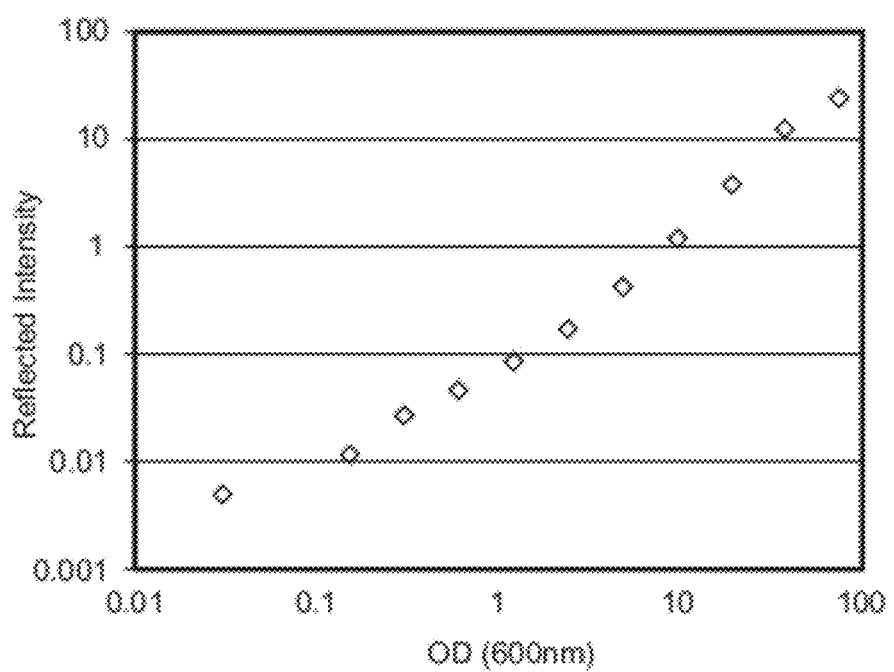
FIG. 9 is a graph of the reflected intensity vs. OD, where the reflected intensity was measured by detector 1 of the sensor embodiment depicted in FIG. 8.

The self-adhesive sensor was attached to the side of a 250 mL PET shake flask filled with 0.9% NaCl and in which various concentrations of Baker's yeast were dissolved. Example measurements collected from the D1 detector as a function of OD are graphed in FIG. 9. In this example, a linear fit to the reflected intensity may not result in sufficiently accurate prediction of OD. Instead, interpolation between adjacent data points could used to provide a calibration. For this purpose a table of ODs at different reflected intensities could be stored in instrument memory. In one embodiment of the sensor calibration, a fitted function is used in some reflectance ranges whereas interpolation is used in other reflectance ranges.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations and permutations, all of which cannot reasonably be recited individually in this document, but can be understood by one of skill in the art on review of this specification.

All publications, patents, patent applications, and/or other documents cited in this application are incorporated by reference in their entirety for all purposes to the same extent as if each individual publication, patent, patent application, and/ or other document were individually indicated to be incorporated by reference for all purposes.

What is claimed is:

1. A method of determining the concentration of particles in a medium, which method comprises:
   providing the medium in a container having a wall;
   irradiating the medium with a light source through the wall with a wavelength of light, wherein the medium absorbs the light as characterized by a mean absorption path length;
   detecting light scattered by the particles in the medium using at least a first detector positioned outside the container wall, wherein the spatial separation between the light source and first detector is within a factor of 10 of the mean absorption path length;
   correlating the detected light to the concentration of the particles.

2. The method of claim 1, wherein the medium is an aqueous medium.

3. The method of claim 1, wherein the container is other than a cuvette or flow cell.

4. The method of claim 1, wherein the container is selected from the group consisting of: a shaker flask, a T-flask, a centrifuge tube, a test tube, a roller bottle, a fermentor, a bioreactor, a stir flask, a carboy, a bag, a media bottle, a multiwell plate, a petri dish, a syringe and a pipette.

5. The method of claim 1, wherein the wavelength of light is an infrared (IR) wavelength.

6. The method of claim 1, wherein the wavelength of light ranges from about 700 nm to about 2000 nm.

7. The method of claim 6, wherein the wavelength is about 1300 nm.

8. The method of claim 1, further comprising selecting a wavelength and sensor geometry so that the spatial separation between the light source and first detector is within a factor of 2 of the mean absorption path length.

9. The method of claim 1, wherein detected light is scattered at an angle ranging from −45 degrees to +45 degrees from the light source to the particle to the detector.

10. The method of claim 1, wherein the light source and detector are aligned parallel to each other.

11. The method of claim 1, wherein the particles are selected from the group consisting of bacteria, animal cells, plant cells, polymer particles, nanoparticles, a sol gel and a virus.

12. The method of claim 1, further comprising providing means of detecting the position or orientation of the light source or detector relative to the container.

13. The method of claim 1, further comprising providing a means of reducing the sensitivity of said determining of the particles concentration to variations in the thickness of said wall.

14. The method of claim 1, further comprising providing a second detector positioned symmetrically with respect to the light source.

15. The method of claim 14, wherein the two symmetrically positioned detectors elements are configured to provide a means of determining whether sufficient medium is present in order to make an accurate measurement of particle concentration.

16. The method of claim 1, wherein the light source and detector are combined in a sensor, wherein a guide is provided for guiding the sensor into a certain alignment with the container.

17. The method of claim 1, further comprising reporting the particle concentration in units of Optical Density (OD).

18. The method of claim 1, wherein the light sources emits light between 1150 and 1350 nm.

19. The method of claim 1, wherein the light sources emits light between 920 and 1150 nm.

20. The method of claim 1, wherein the light sources emits light between 1350 and 1900 nm.

21. The method of claim 1, further comprising monitoring the light source and compensating for changes in radiant flux emitted by the light source, thus stabilizing the light irradiation.

22. The method of claim 1, further comprising tracking a sample identification by using a bar code scanner to read a bar code on the container.

23. The method of claim 1, further comprising subtracting a measurement of blank media from a measurement of the media containing the particle.

24. The method of claim 1, further comprising methods for reducing the influence of ambient noise on the measured signals.

25. The method of claim 24, further comprising the summing of signals over integral numbers of cycles at 50 or 60 Hz.

26. A device for determining the concentration of particles in a medium, which device comprises:
　a) a housing containing a sensor;
　b) a first light source in the sensor, wherein a wavelength emitted by the source is absorbed by the medium, as characterized by a mean absorption path length;
　c) a first detector in the sensor positioned to detect a signal of source light wavelengths scattered by particles within the medium, wherein the spatial separation between the light source and first detector is within a factor of 10 of the mean absorption path length, and
　d) a processor configured to correlate the detected signal to the concentration of particles.

27. The device of claim 26, further comprising a controller configured to control the light sources, and to measure the detected signals.

28. The device of claim 26, wherein power for the device is provided by batteries.

29. The device of claim 26, wherein the housing is configured to be resistant to water ingress.

30. The device of claim 26, wherein the light source is modulated in amplitude or frequency.

31. The device of claim 30, wherein a detector signals measurement rate is at least 4-fold greater than the modulation rate of the light source.

32. The device of claim 30, wherein quadrature slope correction is employed as part of a detector demodulation algorithm.

33. The device of claim 26, wherein the sensor housing is affixed to a vessel, thereby providing the capability of making multiple measurements without the need for reapplication of the sensor to the vessel.

34. The device of claim 26, further comprising a container of media in functional contact with the sensor, wherein the container is selected from the group consisting of: a shaker flask, a T-flask, a centrifuge tube, a test tube, a roller bottle, a fermentor, a bioreactor, a stir flask, a carboy, a bag, a media bottle, a multiwell plate, a petri dish, a syringe and a pipette.

35. The device of claim 26, further comprising one or more additional detectors in functional relation to the light source.

36. The device of claim 35, where signals are combined from two or more paired source-detectors with two different source-detector separations.

37. The device of claim 26, wherein the light source or detectors are fiber optical components which are optically linked to electro-optical components that are physically separated from the housing, wherein the device further comprises one or more additional detectors in functional relation to the light source.

38. The device of claim 26, further comprising a second light source with a light wavelength different from the light wavelength of the first light source.

39. The device of claim 26, wherein the light source wavelength is selected according to the separation between the source and the detector.

40. The device of claim 27, wherein the controller is configured to collect detected signals at least every 0.10 seconds, thereby allowing measurement of variation amount of medium or particles in front of the sensor as it varies over time.

41. The device of claim 26, and the processor is configured to distinguish signals depending on an amount of medium present at the container.

42. The device of claim 26, wherein the media is held in a container and the processor is configured to correlate a ratio of signals collected in the presence of different amounts of media to the media particle concentration.

43. The device of claim 26, wherein the light source and detector are both directed in the same direction.

44. The device of claim 26, wherein the source and detector are aligned within 30 degrees of each other.

45. A method of determining the concentration of particles in a medium which comprises the steps of:
　a) positioning a sensor next to a container having a wall and holding the medium;

b) passing light originating from at least one light source through the container wall into the medium, wherein the light is absorbed by the medium, as characterized by a mean absorption path length;

c) detecting a light signal through the wall with a detector, wherein the signal is from light reflected from within the medium, and wherein the spatial separation between the light source and first detector is within a factor of 10 of the mean absorption path length; and, d) correlating the detected signal to the concentration of the particles in the medium.

* * * * *